United States Patent
Mori et al.

(10) Patent No.: US 6,348,484 B1
(45) Date of Patent: Feb. 19, 2002

(54) STEREOISOMERIC INDOLE COMPOUNDS, PROCESS FOR THE PREPARATION OF THE SAME, AND USE THEREOF

(75) Inventors: Masao Mori, Toyama; Masako Nakagawa; Atsushi Nishida, both of Chiba; Mihoko Fuwa, Komae; Haruo Saito; Takayuki Matsunaga, both of Kanazawa; Satoshi Takahashi, Himi; Chika Hasegawa, Tonami, all of (JP)

(73) Assignee: Lead Chemical Co., Ltd., Toyama (JP)

( * ) Notice: Subject to any disclaimer, the term of this patent is extended or adjusted under 35 U.S.C. 154(b) by 0 days.

(21) Appl. No.: 09/486,318
(22) PCT Filed: Aug. 24, 1998
(86) PCT No.: PCT/JP98/03727
§ 371 Date: Feb. 25, 2000
§ 102(e) Date: Feb. 25, 2000
(87) PCT Pub. No.: WO99/12923
PCT Pub. Date: Mar. 18, 1999

(30) Foreign Application Priority Data

Sep. 5, 1997 (JP) ............................................. 9-241417
Feb. 9, 1998 (JP) ........................................... 10-026979

(51) Int. Cl.[7] ..................... A61K 31/422; C07D 413/04
(52) U.S. Cl. ........................................ 514/374; 548/236
(58) Field of Search ........................... 548/236; 514/374

(56) References Cited

PUBLICATIONS

Nishida et al., CA 129:260620, 1998.*
Annual Report of Toyama Prefectural Pharmaceutical Research Institute, vol. 24, (1997), Sep. 1, 1997, pp. 53–57.
Tetrahedron Letters, 39(33), (1998), Aug. 13, 1998, pp. 5983–5986.
Abstract of Papers, The 116th Annual Meeting of Pharmaceutical Society of Japan (1996) 2, p. 215, upper left column.

* cited by examiner

Primary Examiner—Laura L. Stockton
(74) Attorney, Agent, or Firm—Oliff & Berridge, PLC

(57) ABSTRACT

Novel stereoisomeric indole compounds of the formula (1), a process for the preparation the same, and use thereof

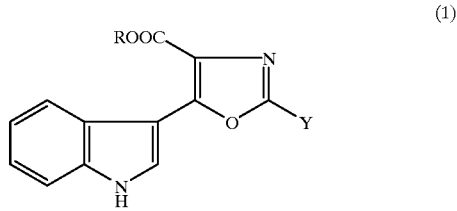

wherein, Y represents the group

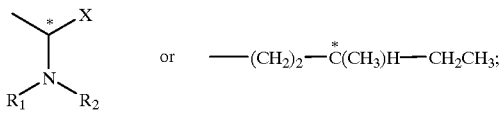

wherein, X represents alkyl group having 1–5 carbon atom(s) (the alkyl group may be substituted with hydroxyl group, carboxyl group, amino group, methylthio group, mercapto group, guanidyl group, imidazolyl group or benzyl group), and $R^1$ and $R^2$ represent each independently hydrogen atom, alkyl group, aralkyl group, cycloalkyl group or aryl group; R represents hydrogen atom, alkyl group, aralkyl group, cycloalkyl group, aryl group, monovalent metal, amine or ammonium; and the symbol '*' represents a position of an asymmetric carbon atom. The above-mentioned compounds can be prepared by condensing tryptophan with a stereoisomeric α-amino acid or carboxylic acid to form an amide form and subjecting or carboxylic acid to form an amide form and subjecting the amide form to oxidative cyclization to form an oxazole ring at once. The compounds exhibit; physiological activities such as inhibitory action against lipid peroxidation, and can be therefore utilized in the form of lipid peroxidation inhibitors containing the same as the active ingredient.

19 Claims, No Drawings

STEREOISOMERIC INDOLE COMPOUNDS, PROCESS FOR THE PREPARATION OF THE SAME, AND USE THEREOF

This application is a 371 of PCT/JP98/03727 filed Aug. 24, 1998.

The present invention relates to novel stereoisomeric indole compounds or salts therof, process for the preparation of the compounds and use of the compounds.

PRIOR ART

An indole compound (tartefragin A) of the following formula which is isolated from an extract of seaweed, "Ayanishiki"(Martensia fragilis Harvey) belonging to, Congregatocarpus family is known [Proceedings of Japan Pharmaceutical Society, the 116$^{th}$ annual meeting, page 2,215 (1996)].

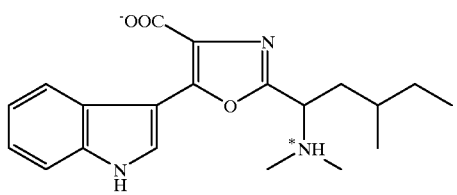

Further, the above-mentioned indole compound is known to have an anti-oxidative action and to have uses including pharmaceutical ones. However, a synthetic method and stereochemistry of the above-mentioned indole compound was not known.

The inventors of the present invention tried first to synthesize stereoisomers of the above-mentioned compound in order to clarify stereostructure, physiological activities and action mechanisms etc. thereof. As a synthetic route for the stereoisomers of the compound, they noticed a route for synthesizing the following L-tryptophan (2) and a stereoisomeric α-amino acid (3a') (hereinafter, the stereoisomeric α-amino acid is referred to as homoisoleucine) as intermediates.

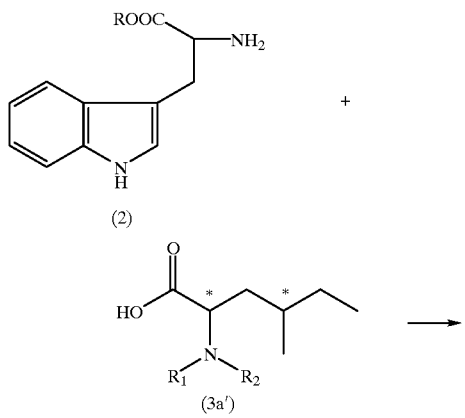

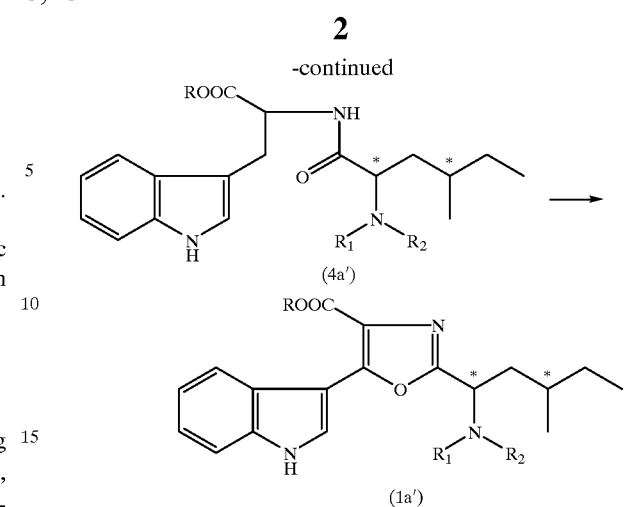

(wherein, R, $R_1$ and $R_2$ have the meanings shown below, and the symbol '*' represents a position of asymmetric carbon atom.)

Since the stereoisomers of the above-mentioned homoisoleucine are not commercially available compounds, they also established a synthetic route described below for the stereoisomers of the homoisoleucine, and furthermore they succeeded to synthesize a stereoisomeric indole compound (1a') from the above-mentioned L-tryptophan (2) and a stereoisomeric homoisoleucine (3a').

Further, from the fact that the synthetic route for the stereoisomeric indole compound (1a') from the above-mentioned L-tryptophan (2) and the stereoisomeric homoisoleucine (3a') was established, in the same manner as in the stereoisomeric homoisoleucine, novel indole alkaloids could be synthesized from L-tryptophan and various α-amino acids other than the stereoisomeric homoisoleucine as starting materials for the purpose of searching compounds having stronger physiological activities than those of the above-mentioned compound (1a'), thus many compounds was obtained.

The inventors also have found that a deamino form of the above-mentioned compound (1a') has higher inhibitory action against lipid peroxidation than any of the four isomers of the above-mentioned Martefragin A, that is (1"S,3"S) form, (1"R,3"S) form, (1"R,3"R) form and (1"S,3"R) form, and also have established synthetic routes thereof.

DISCLOSURE OF THE INVENTION

That is, the present invention relates to stereoisomeric indole compounds of the following formula (1) or salts thereof.

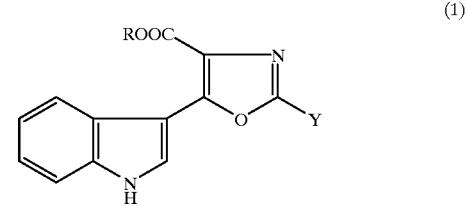

(1)

wherein, Y represents the group:

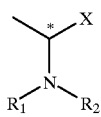

wherein, X represents alkyl group having 1–5 carbon atom(s) (the alkyl group may be optionally substituted with hydroxyl group, carboxyl group, amino group, methylthio group, mercapto group, guanidyl group, imidazolyl group or benzyl group), and $R_1$ and $R_2$ represent each independently hydrogen atom, alkyl group, aralkyl group, cycloalkyl group or aryl group, or Y represents the group

R represents hydrogen atom, alkyl group, aralkyl group, cycloalkyl group, aryl group, monovalent metal atom, amine or ammonium; and the symbol '*' represents a position of an asymmetric carbon atom.

Specifically, there may be mentioned the compound of an amino form of the formula (1a):

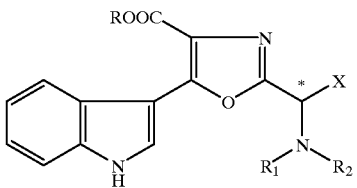

(1a)

or salts thereof as well as the compound of a deamino form of the compound of the formula (1a) of the formula (1b) or salts thereof

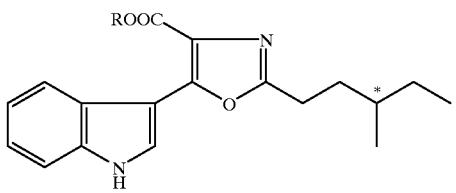

(1b)

wherein, R, $R^1$, $R_2$ and X have the same definitions as the formula (1)

In compounds of the above-mentioned formulae (1), (1a) and (1b), specific examples of suitable substituents are as follows.

In addition to the fact that the substituent R represents hydrogen atom, typical substituents R are straight chained or branched alkyl group having 1–12, particularly 1–6, carbon atom(s), such as methyl group, ethyl group, propyl group, isopropyl group, n-butyl group, tertiary butyl group, pentyl group, hexyl group, octyl group, decyl group and dodecyl group; cycloalkyl group having 5 or 6 ring carbon atoms, such as cyclopentyl group, methylcyclopentyl group, cyclohexyl group and methylcyclohexyl group; aryl group having 6–16 carbon atoms and aralkyl group having 7–16 carbon atoms, such as phenyl group, naphthyl group, benzyl group and phenylethyl group, which may be substituted with halogen atom, hydroxyl group, alkoxy group, amino group and so on. Further, the substituent R may be monovalent metal such as sodium and potassium, amine or ammonium.

Further, suitable substituents $R_1$ and $R_2$ are straight chained or branched alkyl group having 1–12, particularly 1–6, carbon atom(s), such as methyl group, ethyl group, propyl group, isopropyl group, n-butyl group, tertiary butyl group, pentyl group, hexyl group, octyl group, decyl group and dodecyl group; cycloalkyl group having 5 or 6 ring carbon atoms, such as cyclopentyl group, methylcyclopentyl group, cyclohexyl group and methylcyclohexyl group; aryl group having 6–16 carbon atoms and aralkyl group having 7–16 carbon atoms, such as phenyl group, naphthyl group, benzyl group and phenylethyl group, which may be substituted with halogen atom, hydroxyl group, alkoxy group, amino group and so on.

As the salts of the compounds of the formulae (1), (1a) and (1b), there are exemplified salts of inorganic acids and organic acids. However, hydrochloride are particularly preferable.

The indole compounds according to the present invention have one or more asymmetric carbon atom(s), thus form or R form isomers occur depending upon the positions) thereof. For example, in the case of an amino form of the compound (1a'),

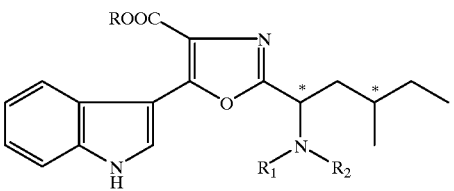

(1a')

it has asymmetric carbon atoms at positions 1" and 3". Therefore, the compounds according to the invention have four isomers respectively for their asymmetric carbon atoms, i.e., (1"S,3"S) form, (1"R,3"S) form, (1"R,3"R) form, (1"S,3"R) form. Further, a deamino form (1b)

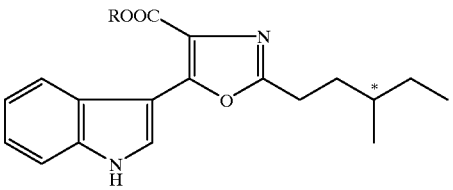

(1b)

of the indole compound according to the invention has an asymmetric carbon atom at position 3". Therefore, the compounds according to the invention have two isomers respectively for their asymmetric carbon atoms, i.e., S form and R form.

The present invention includes all these isomers and mixtures of the isomers.

In the following illustration, the indole compound of the above-mentioned formula (1b) is also referred to as "deaminomartefragin".

The present invention also relates to a process for preparing the stereoisomeric indole compounds of the following formula (1)

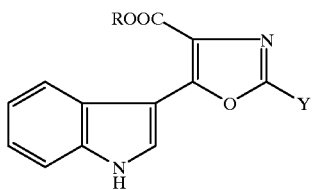
(1)

by condensing tryptophan of the following formula (2)

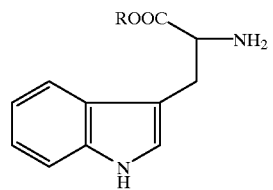
(2)

with an acid of the following formula (3)

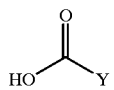
(3)

to obtain a compound of the following formula (4),

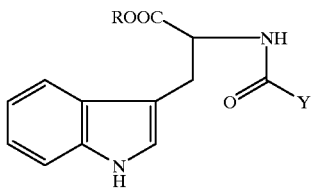
(4)

and subjecting the compound of the formula (4) to cyclization,
wherein, Y represents the group

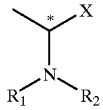

wherein, X represents alkyl group having 1–5 carbon atom(s) (the alkyl group may be substituted with hydroxyl group, carboxyl group, amino group, methylthio group, mercapto group, guanidyl group, imidazolyl group or benzyl group), and $R^1$ and $R^2$ represent each independently hydrogen atom, alkyl group, aralkyl group, cycloalkyl group or aryl group, or Y represents the group

R represents hydrogen atom, alkyl group, aralkyl group, cycloalkyl group, aryl group, monovalent metal atom, amine or ammonium; and the symbol '*' represents a position of an asymmetric carbon atom.

According to this method, the amino form of the stereoisomeric indole compound of the above-mentioned formula (1a) can be prepared by condensing tryptophan of the above-mentioned formula (2) with an acid of the formula (3a)

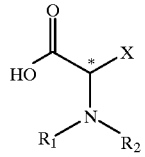
(3a)

to obtain a compound of the following formula (4a),

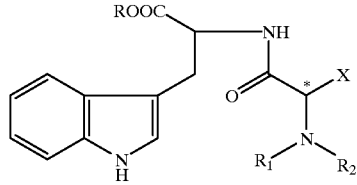
(4a)

and subjecting the compound of the formula (4a) to cyclization, and the deamino form of the stereoisomeric indole compound of the above-mentioned formula (1b) can be prepared by condensing tryptophan of the above-mentioned formula (2) with an acid of the following formula (3b)

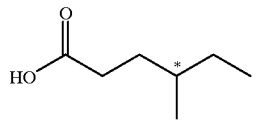
(3b)

to obtain a compound of the following formula (4b),

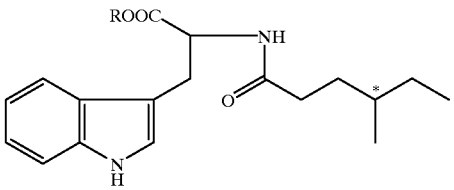
(4b)

and subjecting the compound of the formula (4b) to cyclization, wherein, R, $R_1$, $R^2$ and X have the above-mentioned meanings.

In the compounds of the above-mentioned formulae (2)–(4), (2a)–(4a) and (2b)–(4b), specific examples of suitable substituents are same as those mentioned for the formulae (1), (1a) and (1b).

As described above, the acid used for synthesis of the stereoisomeric indole compounds according to the invention is a stereoisomeric α-amino acid in the case of preparing an amino form and also 4-methylhexanoic acid which is a stereoisomeric carboxylic acid in case of preparing a deamino form.

Typical stereoisomeric α-amino acids include, for example, four stereoisomers of (+)alanine, (+)valine, (−)

leucine, (+)isoleucine, (+)lysine, (−)serine, (−)threonine, (−)phenylalanine, (−)tyrosine, (−)aspartic acid, (+)glutamic acid, (−)methionine, (+)arginine, (−)histidine, (+)ornithine, (+)norleucine, (+)oxyglutamic acid, (−)cysteine and homoisoleucine. Note that four stereoisomers of hoxnoisoleucine are not commercially available, and their synthetic examples are shown below in I. Preparation Examples 1–4 for amino forms of stereoisomeric indole compounds.

4-Methylhexanoic acid has two isomers, which are obtained respectively as intermediates in a synthetic route for (2S,4S)-homoisoleucine in the Preparation Example I and in a synthetic route for (2S,4R)-homoisoleucine in the Preparation example 3 described below.

According to the invention, a stereoisomeric indole compound is prepared by (1) condensing tryptophan with a stereoisomeric α-amino acid or 4-methylhexanoic acid to form an amide, and then (2) subjecting the amide to oxidative cyclization to form an oxazole ring at once by a novel synthetic method For condensation of the tryptophan with the stereoisomeric α-amino acid or 4-methylhexanoic acid, it is preferable to protect an amino group of the α-amino acid. Although there may be mentioned dialkylatione preferably dimethylation, t-butoxycarbonylation and so on for protection of the amino group, it is preferable that when the protecting group being t-butoxycarbonyl group (Boc group) because, particularly, condensation of tryptophan with the stereoisomeric α-amino acid and the subsequent cyclization of the amide are proceeded efficiently.

Further, if the oxidative cyclization of the amide is carried out particularly in the presence of 2,3-dichloro-5,6-dicyanobenzoquinone (DDQ), the cyclization is proceeded efficiently to obtain the cyclized form in a high yield.

For the compounds of the formula (1) according to the invention, it is possible to obtain various kinds of compounds by varying the group Y according to selection of raw materials, i.e., a stereoisomeric α-amino acid and a carboxylic acid, and by varying the substituents R, $R_1$ and $R_2$ according to selection of ester group in the raw material, i.e., tryptophan ester, and selection of the amino substituent of the stereoisomeric α-amino acid, or by changing the substituents in the compounds after synthesis with other substituents R, $R_1$ and $R_2$ different from those.

The novel stereoisomeric indole compounds according to the invention are alkaloids having an indole ring and an oxazole ring, which have inhibitory action against lipid peroxidation, and can be therefore utilized as preventing drugs and therapeutic drugs for circulatory disorders such as arteriosclerosis, hypertension, thrombosis; inflammations such as nephritis; hepatic disorders such as alcoholic hepatitis; digestive disorders such as gastric ulcer; diabetes, carcinogenesis and senescence as well as ultraviolet disorders, and also utilized as ultraviolet disorder preventing materials in cosmetics and the like.

Therefore, the present invention furthermore relates to lipid peroxidation inhibitors containing as the active ingredient the stereoisomeric indole compounds or their salts which are of the above-mentioned formula (1) and exemplified by the formulae (1a) and (1b).

BEST MODE FOR CARRYING OUT THE INVENTION

I. Synthesis For Amino Forms of Stereoisomeric Indole Compounds (Martefragin A and salts or esters thereof)

Synthetic examples of amino forms of indole compounds according to the invention are illustrated as follows. Before synthesis for the compounds according to the invention, syntheses for stereoisomeric homoisoleucine which is raw materials are illustrated in Preparation Examples 1–4, and synthetic examples for stereoisomeric indole compounds by using them are illustrated in Examples

PREPARATION EXAMPLE 1

Synthesis of (2S,4S)-homoisoleucine (2S,4S)-homolsoleucine can be synthesized from optically active methylbutanol or optically active methyliodobutane as starting materials.

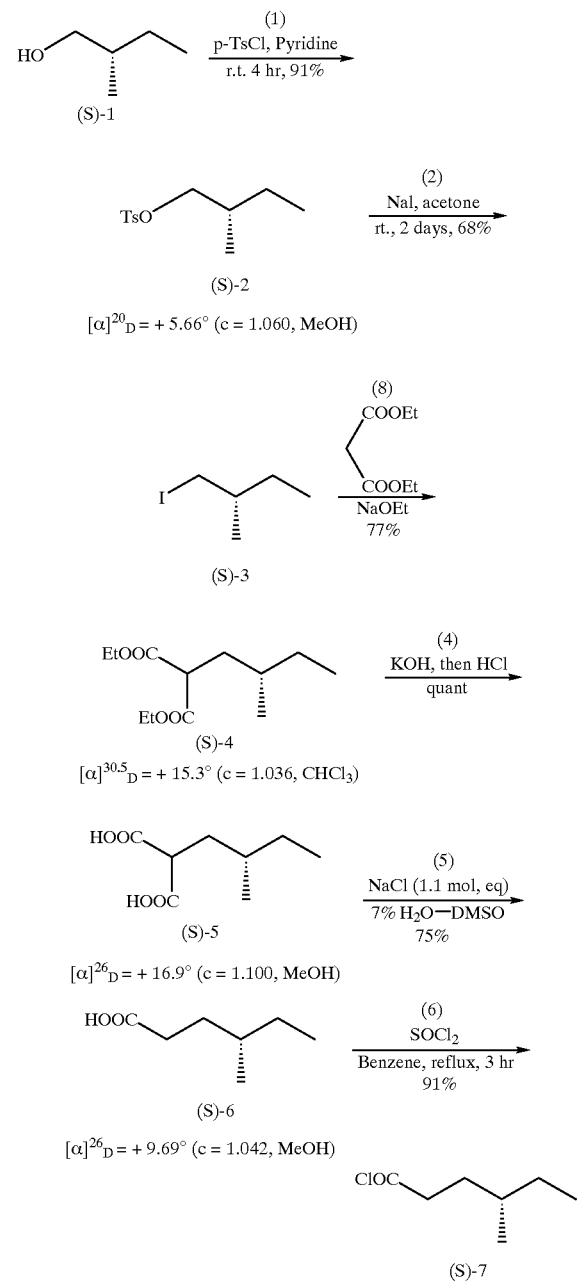

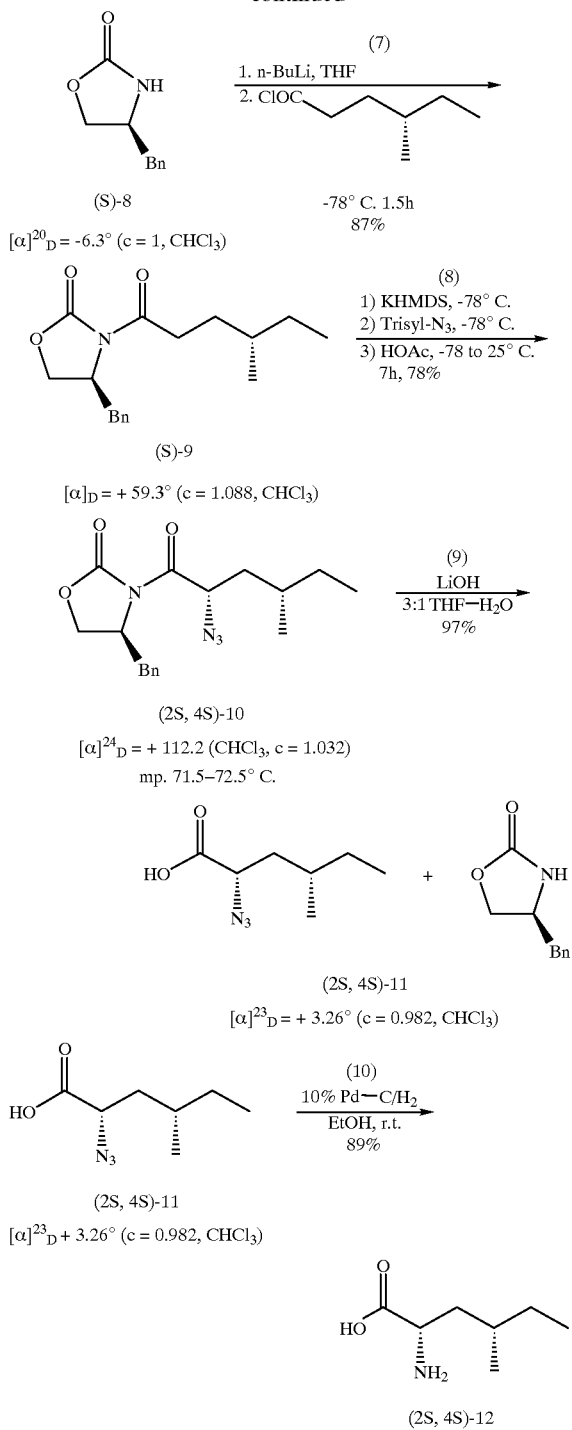

1. Tosylation of optically active methylbutanol (step 1 in Scheme 1)

1 g (11.3 mmol) of (S)-2-methyl-1-butanol: (S)-1 (Tokyo Kasei) and 30 ml of anhydrous pyridine are added into a 100 ml egg plant type flask under an argon atmosphere and stirred at 0° C., and thereafter 4.31 g (22.6 mmol) of p-toluenesulfonyl chloride is added and stirred at 0° C. for 30 minutes, and then stirred at room temperature for 5 hours. Ice water is added and an aqueous layer is adjusted to pH 2–3 with 3N hydrochloric acid and then extracted with diethyl ether. After it is washed with a saturated sodium hydrogencarbonate solution and a saturated saline solution, dried with anhydrous magnesium sulfate, and distilled off the solvent under a reduced pressure, to obtain a colorless oily substance. It is purified with a column chromatography (75 g of $SiO_2$, hexane/ethyl acetate=10:1), to obtain 2.5 g of a tosylated form (S)-2 (a colorless oily substance: yield; 91.41).

$C_{12}H_{18}SO_3$ (M.W.; 242.10), a colorless oily substance, $[\alpha]_n^{20}+5.66$ (C=1.060, MeOH)

2. Iodation of tosylated form (S)-2 (step 2 in Scheme 1)

1.94 g (S mmol) of the tosylated form (S)-2 and 30 ml of anhydrous acetone are added into a 100 ml egg plant type flask under an argon atmosphere, shielded from light, and thereafter 2.4 g (16 mmol) of sodium iodide is added. After stirring at room temperature for 2 days, pentane is added to dilute the reaction solution and cooled to precipitate its sodium salt. After the sodium salt is removed with a glass filter, it is extracted with water to remove acetone, dried with anhydrous magnesium sulfate and distilled off pentane under the normal pressure, to obtain 1.08 g (yield; 68.0%) of an iodated form (S)-3. The structure thereof is confirmed by comparison with a commercially available one.

3. Synthesis of ester malonate using iodated form (S)-3 (step 3 in Scheme 1)

1.38 g of metallic sodium and 50 ml of anhydrous ethanol are added into a 200 ml three-necked flask under an argon atmosphere at 0° C. and stirred. After sodium is all dissolved, 9.45 ml of diethyl malonate is added dropwise by a syringe, and then 6.5 ml of the iodated form (S)-3 is added dropwise and stirred at room temperature overnight. 100 ml of an aqueous ammonium chloride solution is added, ethanol is removed by distillation under a reduced pressure, and the residue is extracted with diethyl ether. An ether layer is washed with a saturated saline solution, thereafter dried with anhydrous magnesium sulfate, and distilled off the solvent under a reduced pressure, to obtain a colorless oily substance, It is purified with a column chromatography (200 g of $SiO_2$ for flash, hexane/ethyl acetate 30:1), to obtain 8.80 g (yield; 76.5%) of a diester form (S)-4.

$C_{12}H_{22}O_4$ (M.W.; 230.15), a colorless oily substance, $[\alpha]_D^2+15.3$ (C=1.060, MeOH)

4. Hydrolysis of diester form (S)-4 (step 4 in Scheme 1)

6.90 g of the diester form (S)-4 and 20 ml of ethanol are added into a 300 ml egg plant type flask and stirred. 5.71 g (102 mmol) of potassium hydroxide dissolved beforehand in 100 ml of water is added and heated at reflux. The temperature of the solution is returned to room temperature and ethanol is removed by distillation under a reduced pressure, and thereafter impurities are removed by extraction with ethyl acetate. After 3N HCl is added to an aqueous layer to adjust to pH 1–2, the layer is extracted with ethyl acetate. An organic layer is salted out with sodium chloride, dried with anhydrous magnesium sulfate and thereafter distilled off the solvent under a reduced pressure, to obtain 5.22 g (yield; 100%) of an intended compound, a dicarboxylic acid (S)-5.

$C_8H_{14}O_4$ (M.W.; 174.09), white powders, $[\alpha]_D^{26}+16.9$ (C=1.10, MeOH)

5. Decarboxylation of dicarboxylic acid (S)-5 (step 5 in Scheme 1)

5.05 g (29 mmol) of the dicarboxylic acid (S)-5, 16 ml of a 7% aqueous DMSO solution and 1.87 g (32 mmol) of sodium chloride are added into a 50 ml egg plant type Cask, and heated at 150–175° C. for 4 hours. The temperature of the solution is returned to room temperature and extracted twice with diethyl ether, and an organic layer is washed with water. It is dried with anhydrous magnesium sulfate and distilled off the solvent under a reduced pressurer to obtain a colorless oily substance. It is purified with a column chromatography (120 g of SiO$_2$, pentane/diethyl ether=5:1), to obtain 2.82 g (yield; 75%) of an intended carboxylic acid (S)-6. The (S)-6 is a raw material for synthesis of deaminomartefragin described below.

C$_7$H$_{14}$O$_2$ (M.W.; 130.10), colorless and oily, $[\alpha]_D^{26}$+9.69 (C=1.042, MeOH)

6. Synthesis of acid chloride (S)-7 (step 6 in Scheme 1)

2.82 g of the carboxylic acid (S)-6, 18.0 ml of anhydrous benzene and 9.0 ml of thionyl chloride are added into a 50 ml egg plant type flask and heated at reflux for 3 hours. The temperature of the solution is returned to room temperature and thereafter distilled off the solvent under a reduced pressure, to obtain 2.92 g (yield; 91%) of an acid chloride (S)-7. The (S)-7 is subjected to condensation with an asymmetrical assistant group (S)-8 without any purification after confirming absorption of the carbonyl group assigned to the acid chloride by IR spectrum. C$_7$H$_{13}$Cl (M.W.; 148.55), colorless and oily.

7. Condensation with asymmetic assistant group (S)-8 (step 7 in Scheme 1)

3.85 g (21.7 mmol) of (4S)-benzyloxazolidinone and 50 ml of anhydrous (THF) are added into a 200 ml three-necked flask under an argon atmosphere and cooled to −78° C. 13.6 ml of a 1.6M n-butyl lithium/n-hexane solution is added and stirred at −78° C. for 40 minutes, and 2.92 g (19.7 mmol) of the acid chloride (S)-7 is added and stirred at −78° C. for 1.5 hours. An aqueous ammonium chloride solution is added, and the solution is extracted with diethyl ether, washed with a saturated saline solution, dried with anhydrous magnesium sulfate, and thereafter distilled off the solvent under a reduced pressure, to obtain a colorless oily substance. It is purified with a column chromatography (45 g of SiO$_2$, hexane/ethyl acetate=5:1), to obtain 4.93 g (yield; 86.5%) of an intended compound (S)-9, as colorless crystals.

C$_{17}$H$_{23}$NO$_3$ (M.W.; 289.29), white powders, $[\alpha]_D^{27}$+59.3 (C=1.088, CHCl$_3$)

8. Direct azidation to carboxyimide (step 8 in Scheme 1)

1.03 g (5.19 mmol) of potassium ditrimethylsilylamide and 10 ml of anhydrous THF are added into a 100 ml two-necked flask under an argon atmosphere and made to −78° C. 1 g (3.46 mmol) of (S)-9 dissolved beforehand in 10 ml of anhydrous THF is added by a cannula and stirred at −78° C. for 30 minutes. Furthermore, 1.35 g (4.36 mmol) of triisopropyl benzenesulfonylazide dissolved beforehand in 6 ml of anhydrous THF is added by a cannula and stirred for 2 minutes, and thereafter 0.91 ml (15.9 mmol) of glacial acetic acid is added. It is stirred at room temperature for 7 hours. The reaction solution is diluted with ethyl acetate, to which a saturated saline solution is added and extracted twice with ethyl acetate. It is washed with a saturated sodium hydrogencarbonate, dried with anhydrous sodium sulfate, and distilled off the solvent under a reduced pressure, to obtain 1.85 g of a yellow oily substance. It is purified with a column chromatography (60 g of SiO$_2$. for flash, hexane/dichloromethane=3:1), to obtain 893 mg (yield; 78.1%) of an intended azide form (2S, 4S)-10.

C$_{17}$H$_{22}$N$_4$O$_3$ (M.W.; 330.39), colorless crystals, mp.; 71.5–72.5° C., $[\alpha]_D^{24}$+112.2 (C=1.032, CHCl$_3$)

9. Removal of asymmetrical assitant group [Synthesis of α-azide carboxylic Acid (2S, 4S-11] (step 9 in Scheme 1)

850 mg of the azide form (2S, 4S)-10 and 50 ml of 75% THF are added into a 200 ml egg plant type flask under an argon atmosphere and made to 0° C., and 216 mg of lithium hydroxide monohydrate is added and stirred for 1 hour. An aqueous saturated sodium hydrogencarbonate solution is added, distilled off THF under a reduced pressure, and thereafter extracted with ethyl acetate. An ethyl acetate layer is dried with anhydrous sodium sulfate and distilled off the solvent under a reduced pressure, to recover 450 mg (yield; 99%) of (S)-8. An aqueous layer is adjust to pH 1–2 with 3N hydrochloric acid and extracted with ethyl acetate, and an ethyl acetate layer is dried with anhydrous sodium sulfate and distilled off the solvent under a reduced pressure, to obtain 425 mg (yield; 96.7%) of an intended α-azide carboxylic acid (2S,4S)-11 as an colorless oily substance.

C$_7$H$_{13}$N$_3$O$_2$ (M.W.; 171.101), a colorless oily substance, $[\alpha]_D^{23}$+3.26 (C=0.982, CHCl$_3$)

10. Reduction of α-azide carboxylic acid: Synthesis of (2S,4S)-homoisolencine (step 10 in Scheme 1)

378 mg (2.21 mmol) of the α-azide carboxylic acid (2S,4S)-11, 4.0 ml of anhydrous ethanol and 37.8 mg of 10% Pd-C are added into a 25 ml egg plant type flask under an argon atmosphere with hydrogen displacement and stirred at room temperature for 2.5 hours. Pd-C is removed by filtration and the solvent is distilled off under a reduced pressure, to obtain 285 mg (yield; 88.9%) of (2S,4S)-12 [(2S,4S)-homoisoleucine] as colorless crystals.

C$_7$H$_{15}$NO$_2$ (M.W.; 145.1103), colorless crystals, IR: ν [cm$^-$]=2962, 2920, 1584, 1513, 1405, 669, 554, 471 LRE-IMS: m/z (%) 154(M$^+$, 1), 100(100) HREIMS Calcd for C$_7$H$_{15}$NO$_2$: 145.1103, Found 145.1127

PREPARATION EXAMPLE 2

Synthesis of (2R,4S)-homoisoleucine

The steps to the acid chloride (S)-7 are the same as the above-mentioned Preparation Example 1. The asymmetrical assistant group used has R-configuration. The reaction steps after the condensation with the asymmetrical assistant group are carried out similarly to Preparation Example 1. The reaction steps from the condensation with the asymmetrical assistant group to synthesis of (2R,4S)-homoisoleucine [(2R,4S)-23] and physical data for (2R,4S)-homoisoleucine are shown as follows.

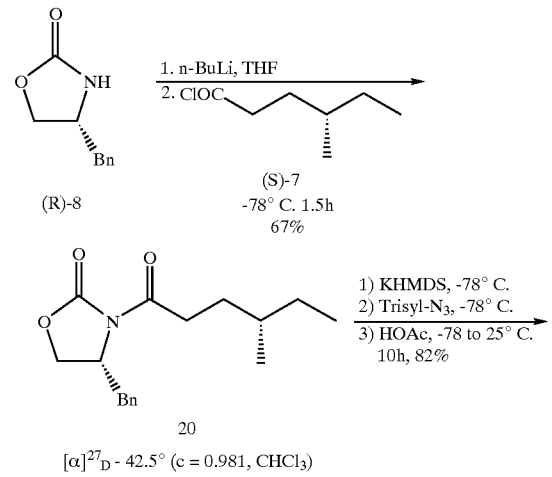

Scheme 2: Synthetic route of (2R, 4S) - homoisoleucine

-continued

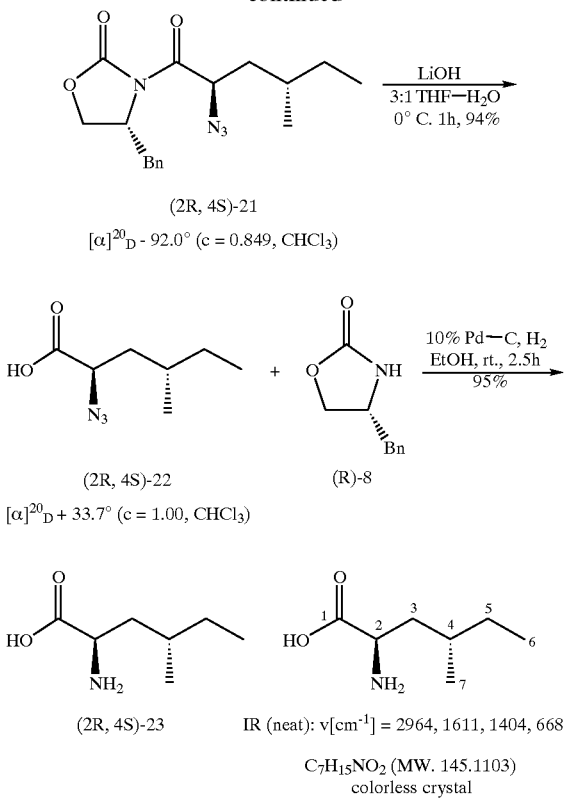

PREPARATION EXAMPLE 3

Synthetic route of (2S,4R)-homoisoleucine (2S,4R)-homoisoleucine is synthesized from (S)-citronellol as a starting material.

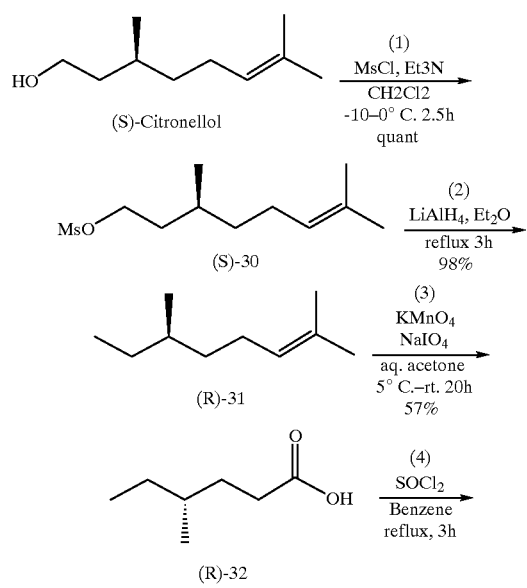

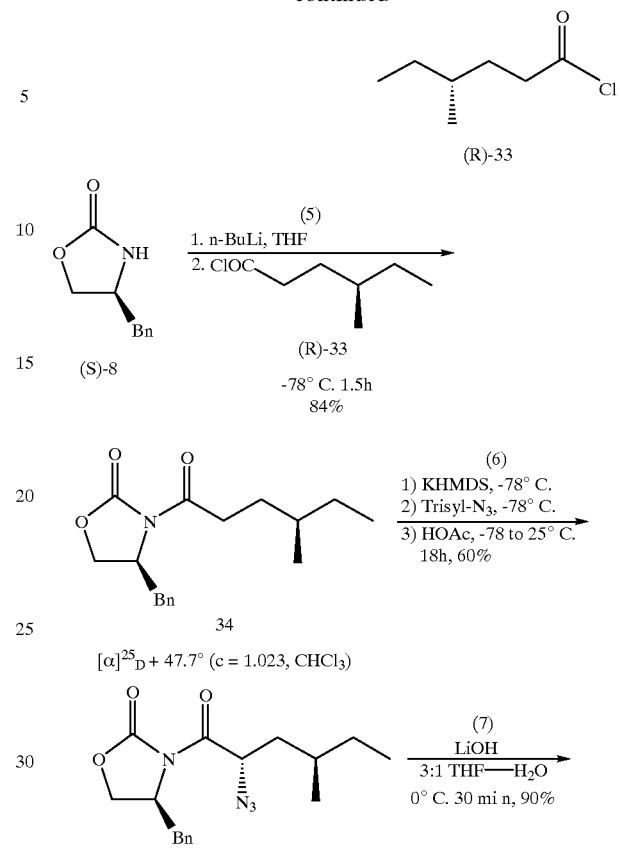

1. Mesylation of (S)-citronellol (step 1 in Scheme 3)

5 g (32.0 mmol) of (5)-citronellol, 180 ml of dichloromethane and 4.86 g (35.2 mmol, 1.1 eq) of triethylamine are added into a 500 ml three-necked flask under an argon atmosphere and cooled with ice to −10° C., and thereafter 4.03 g (35.2 mmol, 1.1 eq) of mesyl chloride is added dropwise. After the reaction solution is stirred at −10 to 0° C. for 2.5 hours, it is washed with ice water, 5% hydrochloric acid and water, dried with anhydrous sodium sulfate and distilled off the solvent under a reduced pressure, to obtain a colorless oily substance (S)-30. It is subjected to the next reduction without any purification.

2. Reduction of mesylate (S)-30 (step 2 in Scheme 3)

400 ml of diethyl ether and 1.80 g (47.3 mmol, 1.4 eq) of lithium aluminum hydride are added into a 200 ml three-necked flask equipped with a calcium chloride tube and a reflux condenser and cooled with ice. A solution of 7.92 g (33.8 mmol) of (S)-30 in diethyl ether is added dropwise and heated at reflux for 3 hours. After completion of the reaction, the reaction solution is cooled with ice, and 3.6 ml of water is added and stirred for 1 hour, additional 2.88 ml of a 10% aqueous sodium hydroxide solution is added and stirred for 1 hour thereafter filtered off by Celite to remove lithium aluminum hydride and distilled off the solvent under a reduced pressure, to obtain 4.5 g (98%) of a colorless oily substance (R)-31.

3. Oxidation of (R)-31 (step 3 in Scheme 3)

24.7 g (115.6 mmol, 3.6 eq) of sodium periodate and 175 ml of an aqueous acetone solution (acetone:water=70:105) are added to suspend in a 500 ml three-necked flask under an argon atmosphere. A solution of 4.5 g (32.1 mmol) of (R)-31 in acetone is added dropwise and made to 5° C. 40 ml of a solution of 0.86 g (5.46 mmol, 0.17 eq) of potassium permanganate in water and 40 ml of acetone are added dropwise simultaneously. They are stirred at from 5° C. to room temperature for 20 hours. A reddish brown residue is removed by filtration with Celite, and acetone is distilled off under the normal pressure. 1N sodium hydroxide is added to the residue to make basic, which is extracted with diethyl ether to remove solubles. An aqueous layer is acidified with 3N hydrochloric acid, extracted with diethyl ether, dried with anhydrous sodium sulfate and distilled off the solvent under a reduced pressure, to obtain a colorless oily substance. It is purified with a column chromatography (50 g of $SiO_2$, hexane/ethyl acetate=5:1), to obtain 2.389 g (57%) of (R)-32. The (R)-32 is a raw material for synthesis of deaminomartefragin described below.

4. Steps (4)–(8) in Scheme 3

Steps (4)–(8) in Scheme 3 are carried out similarly to steps (6)–(10) in Preparation Example 1. Physical data of the obtained (2S,4R)-homoisoleucine [(2S,4R)-37] are as follows.

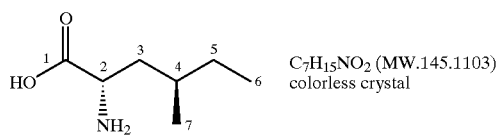

$C_7H_{15}NO_2$ (MW.145.1103)
colorless crystal

IR (neat): ν [$cm^{-1}$]=2964, 1587, 1404

PREPARATION EXAMPLE 4

Synthesis of (2R,4R)-homoisoleucine

Steps to the acid chloride (R)-33 are same as the above-mentioned Preparation Example 3. The steps after the condensation with an asymmetric assistant group by using R-configuration asymmetric assistant group are carried out similar to the Preparation Example 1.

The steps from the condensation with the asymmetrical assistant group to synthesis of (2R,4R)-homoisoleucine [(2R,4R)-47] and physical data for (2R4R)-homoisoleucine are shown as follows.

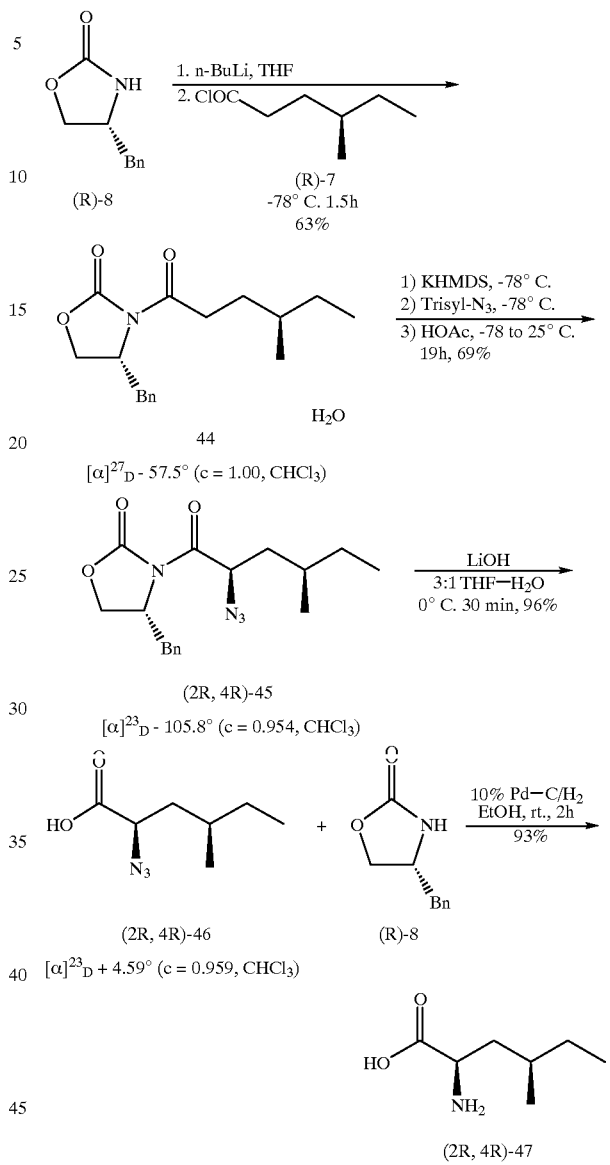

Scheme 4: Synthetic route of (2R, 4R)-homoisoleucine

Next, synthetic examples of stereoisomeric indole compounds from tryptophan ester and stereoisomeric homoisoleucine are shown.

EXAMPLE 1

Synthesis of (1"S,3"S)-indole

Scheme 5: Synthetic route of (1" S, 3" S) - indole

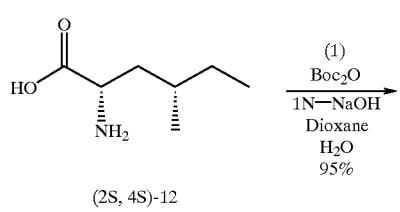

-continued

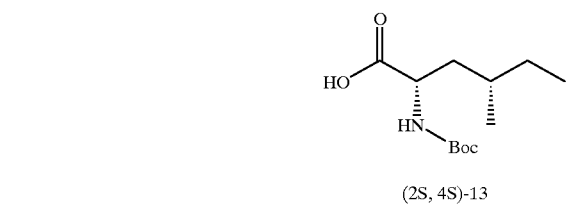

(2S, 4S)-13

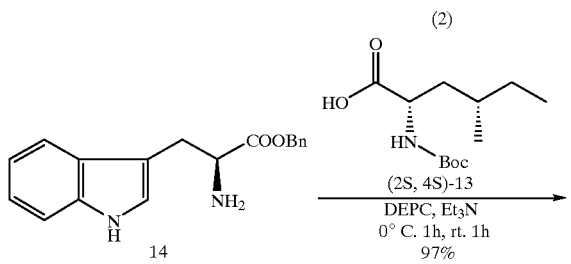

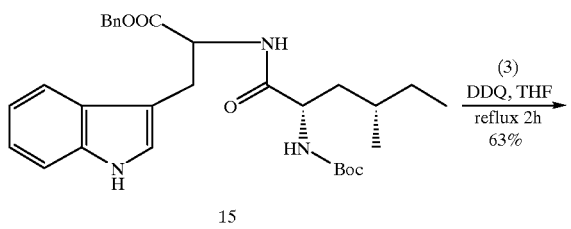

(1″ S, 3″ S)-16

$[\alpha]^{16}{}_D$ - 39.01° (c = 0.810, CHCl$_3$)
mp. 210.5–211.5° C.

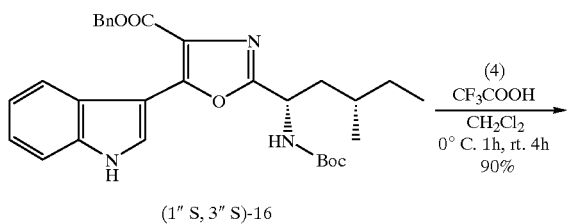

(1″ S, 3″ S)-17

$[\alpha]^{20}{}_D$ - 16.42° (c = 0.682, CHCl$_3$)
mp. 169.5–170.5° C.

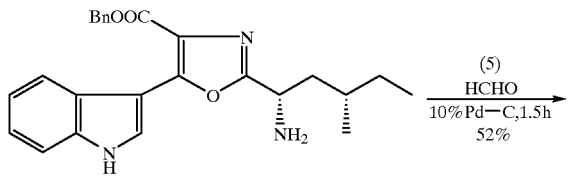

(1″ S, 3″ S)-18

-continued

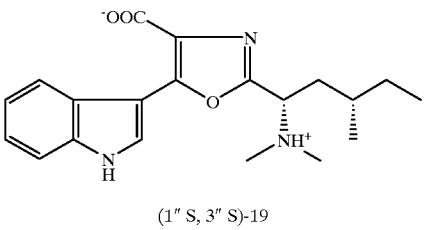

(1″ S, 3″ S)-19

1. t-Butoxycarbonylation of (2S, 4S)-homoisolenine (step 1 in Scheme 5)

1285 mg (1.96 mmol) of (2S,4S)-homoisoleucine obtained in Preparation Example 1, 2.5 ml of a 1N aqueous sodium hydroxide solution, 1.5 ml of water, 1.5 ml of dioxane and 643 mg (2.95 mmol) of Boc$_2$O are added into a 25 ml egg plant type flask and stirred at room temperature for 16 hours. An aqueous saturated sodium hydrogencarbonate solution is added and washed with diethyl ether, and thereafter an aqueous layer is acidified (to about pH3) and extracted twice with diethyl ether. It is washed with water, dried with anhydrous sodium sulfate and distilled off the solvent under a reduced pressure, to obtain 456 mg (yield; 95%) of (2S,4S)-13 ) Boc form of (2S,4S)-homoisoleucine as a colorless oily substance.

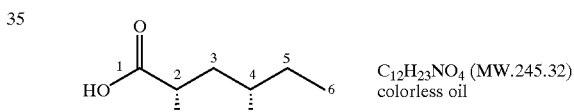 $C_{12}H_{23}NO_4$ (MW.245.32)
colorless oil

IR (neat) ν [cm$^{-1}$]=2965, 1724, 1516, 1456, 1252, 1165, 1051, 1024, 852, 779.

2. Condensation of tryptophan-O-benzyl ester and Boc form of (2S,4S)-homoisoleucine (step 2 in Scheme 5)

325 mg of L-tryptophan benzyl ester, 30 ml of anhydrous THF and 265 mg of the Soc form of homoisolencine [(2S,4S)-13] are added into a 100 ml two-necked egg plant type flask under an argon atmosphere and made to 0° C. 0.3 ml of a condensing agent, DEPC (diethylphosphoryl cyanide) and 0.33 ml of triethylamine are added dropwise by a syringe and stirred at 0° C. for 1 hour, then at room temperature for 1 hour. Ethyl acetate is added, dried with saturated sodium hydrogencarbonate and distilled off the solvent under a reduced pressure, to obtain a brown oily substance. It is purified with a column chromatography (20 g of SiO$_2$, hexane/ethyl acetate=2:1), to obtain 493.7 mg (yield; 97%) of an intended condensate, dipeptide-15, as a amorphous state. It is recrystallized from ethyl acetate and hexane.

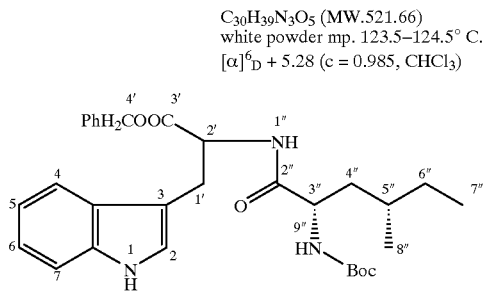

$C_{30}H_{39}N_3O_5$ (MW.521.66)
white powder mp. 123.5–124.5° C.
$[\alpha]^6_D$ + 5.28 (c = 0.985, $CHCl_3$)

IR(KBr): ν [cm$^{-1}$]=3365, 2962, 1734, 1684, 1647, 1520, 1458, 1437, 1275, 1256 1160, 741

$^{13}$C-NMR (400 MHz, $CDCl_3$): 172.15(s), 171.42(S). 155.44(s), 13624(s), 135.32(s),
128.50(s), 128.32(s), 127.72(s), 123.07(s), 122.19(s), 119.67(s), 118.65(s), 111.23(s), 109.84(s), 80.01(s), 67.13(s), 53.08(s), 39.59(s), 30.07(s), 28.70(s), 28.29 (s),
27.79(s), 19.27(s), 10.84(s)

LRFABMS: m/z(%) 522(M+H$^+$, 20), 130(100)

HRFABMS Calcd for $C_{30}H_{39}N_3O_5$+H: 522,2968. Found: 522.2957

$^1$H-NMR (400 MHz, $CDCl_3$): δ 8.14 (1H, b, 1—H)
  δ 751 (1H, d, J=7.6, 7—H)
  δ 7.28~6.85 (9H, m, Aromatic Hs)
  δ 652 (1H, d, 2—H)
  δ 5.04 (2H, s, 4'—H)
  δ 4.93 (1H, m, 2'—H)
  δ 4.82 (1H, b, 9"—H)
  δ 4.07 (1H, s, 3"—H)
  δ 3.29 (2H, m, 1'—H)
  δ 1.72 (1H, m, 5"—H)
  δ 1.40 (9H, s, BOC—Hs)
  δ 1.28 (2H, m, 4"—H)
  δ 1.07(1H, m,)
  δ 0.84 (6H, m, 6"—H, 7"—H)

3. DDQ oxidation of dipeptide-15 (step 3 in Scheme 5)

300 mg (0.60 mmol) of dipeptide-15, 30 ml of anhydrous THF and 313 mg (1–38 mmol) of DDQ (2,3-dichloro-5,6-dicyanobenzoquinone) are added into a 100 ml egg plant type flask under an argon atmosphere and heated at reflux for 1 hour. The temperature of the solution is returned to room temperature and distilled off THFunder a reduced pressure, and thereafter water is added and extracted with ethyl acetate. An ethyl acetate layer is washed with an aqueous saturated sodium hydrogencarbonate solution and a saturated saline solution and dried with anhydrous magnesium sulfate. The solvent is distilled off under a reduced pressure, to obtain a brown solid. It is purified with a column chromatography (10 g of $SiO_2$ for flash, hexane/ethyl acetate=3:1), to obtain 224 mg (yield; 62.5%) of an intended cyclized form 1"S,3"S)-16.

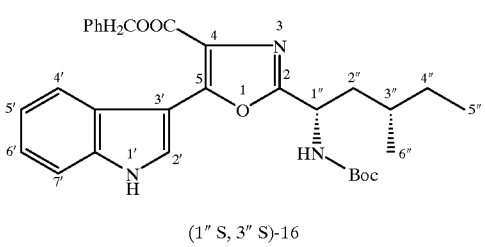

$C_{30}H_{35}N_3O_5$ (MW.517.6261)
colorless pouder mp. 210.5–211.5
$[\alpha]^{16}_D$ - 39.01 (c = 0.810, $CHCl_3$)

(1" S, 3" S)-16

IR (KBr): ν[cm$^{-1}$=]3278, 2964, 1689, 1593, 1280, 1245, 1188, 1074, 741, 696

$^1$H-NMR (400 Mhz, $CDCl_3$): δ 8.66 (1H, b, 1'N—H)
  δ 8.60 (1H, s, 2'—H)
  δ 8.13 (1H, d, J=7.8, 7'—H)
  δ 7.45 (3H, m, 4'~6'—H)
  δ 7.24–738 (5H, m, —Ph)
  δ 5.32 (2H, dd, J=12.5, 16.4, —$CH_2Ph$)
  δ 5.28 (1H, d, 1"—H)
  δ 5.10 (1H, d, N—H)
  δ 1.74 (1H, m, 2"—H)
  δ 1.52 (2H, m. 4"—H)
  δ 1.45 (9H, s, BOC—H)
  δ 1.22 (1H, m, 3"—H)
  δ 0.99 (3H, d, J=6.6, 6"—H)
  δ 0.88 (3H, t, 1J=7.3, 5"—H)

LRFASMS: m/z(%) 518(M$^+$+H, 100)

HRFABMS Calcd for $C_{30}H_{35}N_3O_5$+K 518.2655. Found: 518.2639

Anal. Calcd For $C_{30}H_{39}N_3O_5$: C69.6, HB6.8Z, N8.12 Found: C68.35, H6.83, N7.74

4. De-t-butoxycarbonylation of cyclized form (1"S,3"S)-16 (step 4 in Scheme 5)

16.80 mg (0.15 mmol) of the cyclized form (1"S,3"S)-16 and 2 ml of dichloromethane are added into a 30 ml two-necked flask under an argon atmosphere and cooled to 0° C. 0.5 ml of trifluoroacetic acid is added, stirred at 0° C. for 1 hour, and thereafter stirred at room temperature until the raw materials being disappeared. It is cooled again to 0° C. and neutralized with an aqueous saturated sodium hydrogencarbonate solution, removed off the solvent by distillation under a reduced pressure and extracted with ethyl acetate. An organic layer is washed with an aqueous saturated sodium chloride solution, dried with anhydrous sodium sulfate and thereafter distilled off the solvent under a reduced pressure, to obtain 59 mg (yield; 91%) of an amine form (1"S,3"S)-17 as a brown solid. It is recrystallized from ethyl acetate ester and hexane.

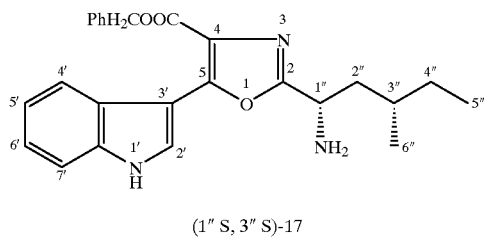

C$_{25}$H$_{27}$N$_3$O$_3$ (MW.417.5081)
brown crystyal mp. 169.5–170.5
[α]$^{20}_D$ - 16.4 (c = 0.68, CHCl$_3$)

(1″ S, 3″ S)-17

IR (KBr): ν [cm$^{-1}$]=3143, 2962, 1707, 1593, 1280, 1244, 1074, 741, 698

$^1$H-NMR (400 Mhz CDCl$_3$): δ 9.20 (1H, b, 1′N—H)
δ 8.67 (1H, d, J=2.7, 3′—H)
δ 8.11 (1H, m, 7′-H)
δ a 7.42 (3H, m, 4~6′—H)
δ 7.29 (5H, m, —Ph)
δ 5.42 (2H, s, —CH$_2$Ph)
δ 4.26 (1H, b, 1″—H)
δ 2.03 (1H, m, 2′—H)
δ 1.76 (2H, b, N—H)
δ 1.69 (1H, m, 4″—H)
δ 1.51 (H, m, 4″—H)
δ 1.21 (1H, m, 3″—H)
δ 0.97 (3H, d, J=6.6, 6″—H)
δ 0.87 (3H, t 7.5, 5″—H)

LRFABMS: m/z(%) 417(M$^+$, 85), 401(100)
HRFABMS Cald for C$_{25}$H$_{27}$N$_3$O$_3$+H: 418.2131. Found: 418.2115
Anal. Calcd for C$_{25}$N$_3$O$_3$: C71.92, H6.52, N10.06 Found C71.99, H6.62, N10.25

5. Dimethylation of amine form (1″S,3″S)-17 (step 5 in Scheme 5)

85 mg (0.20 mmol) of the amine form (1″S,3″S)-17, 3.4 ml of a 37% formaldehyde solution, 1.7 ml of acetic acid and 3.0 ml of 1,4-dioxane are added into a 25 ml egg plant type flask under an argon atmosphere and also 85 mg of 10% Pd-C is added with ice cooling. Hydrogen displacement is carried out and stirring is continued at room temperature until the raw materials being disappeared (about 1.5 hours). Ethanol is added, Pd-C is removed by filtration, and the solvent is distilled off under a reduced pressure, to obtain 466 mg of a colorless oily substance It is purified with a column chromatography (15 g of silica gel for flash, hexane/ether=1:5), to obtain 4.7 mg (yield; 53%) of a dimethyl form (1″S,3″S)-18 as a colorless oily substance.

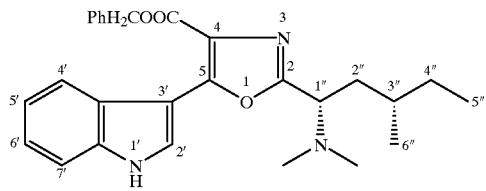

C$_{27}$H$_{31}$N$_3$O$_3$ (MW.445.5617)
colorless oil (1″ S, 3″ S)-18

IR (neat): ν (cm$^{-1}$=330, 2962, 1701, 1589, 742, 702
$^1$H-NMR(400 MHz, CDCl$_3$): δ 9.36 (1H, b, 1′N—H)
δ 8.71 (1H, d, J=2.9, 2′—H)
δ 8.16 (1H, m, 7′—H)
δ 7.42 (3H, m, 4′–6′—H)
δ 7.28 (5H, m, —Ph)
δ 5.42 (2H, dd, J=12.4, 163, —CH$_2$Ph)
δ 4.01 (1H, dd, J=5.3, 9.7. 1″—H)
δ 2.39 (6H, s, N(CH$_3$)$_2$)
δ 2.21 (1H, m, 2″—H)
δ 1.72 (1H, m, 2″—H)
δ 1.39 (1H, m, 4″—H)
δ 1.26 (1H, m, 4″—H)
δ 1.19 (1H, m, 3″—H)
δ 0.93 (3H, d, J=6.6, 6″—H)
δ 0.84 (3H, t, J=7.3. 5″—H)

LAFABMS: m/z(%) 446(M$^+$+H, 15), 401(100)
HRFABMS Calcd for C$_{27}$H$_{31}$N$_3$O$_3$+H: 446.2444 Found 446.2449

6. Debenzylation of dimethyl form (1″S,3″S)-18 (step 6 in Scheme 5)

44 mg (0.0988 mmol) of the dimethyl form (1″S,3″S)-18 and 4 ml of ethyl acetate are added into a 25 ml egg plant type flask under an argon atmosphere and cooled with ice, and 44 mg of 10% Pd-C is added. Hydrogen displacement is carried out and stirring is continued at room temperature until the raw materials being disappeared. Ethanol is added and Pd-C is removed by filtration, and the solvent is distilled off under a reduced pressure, to obtain a colorless solid. It is purified with a column chromatography (1 g of SiO$_2$, CHCl$_3$/MeOH/NH$_4$H=7:3:03), to obtain 10 mg (yield; 57.4%) of (1″S,3″S)-19.

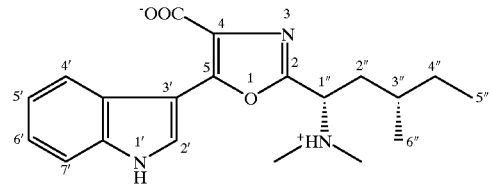

C$_{20}$H$_{25}$N$_3$O$_3$ (MW.355.4373)
colorless powder mp. 163–164

(1″ S, 8″ S)-19

IR(KBr): ν [cm$^{-1}$]=3430, 2962, 1595, 1458, 1389, 744
$^1$H-NMR (400 MHz, CDCl$_3$): δ 8.60 (1H, b, 2′—H)
δ 8.01 (1H, d, 7′—H)
δ 7.33 (1H, dd, J=1.0, 7.6, 4′—H)
δ 7.05 (2H, m, 5′, 6′—H)
δ 4.24 (1H, dd, J=4.5, 11.0, 1″—H)
δ 2.36 (1H, ddd, J=10.5. 10.5, 2.7)
δ 1.74 (1H, m 2″—H)
δ 1.36 (1H, m, 4″—H)
δ 1.26 (1H, m, 3″—H)
δ 1.18 (1H, m, 4″—H)
δ 0.96 (3H, d, J=6.4, 6″—H)
δ 0.84(3H, t, J=7.1, 5,″—H)

EXAMPLE 2

Synthesis of (1″R,3″S)-indole

Similar to Example 1, (1″R,3″S)-indole is prepared from tryptophan ester and (2R,4S)-homoisoleucine in the Preparation Example 2. The synthetic route thereof is illustrated as follows.

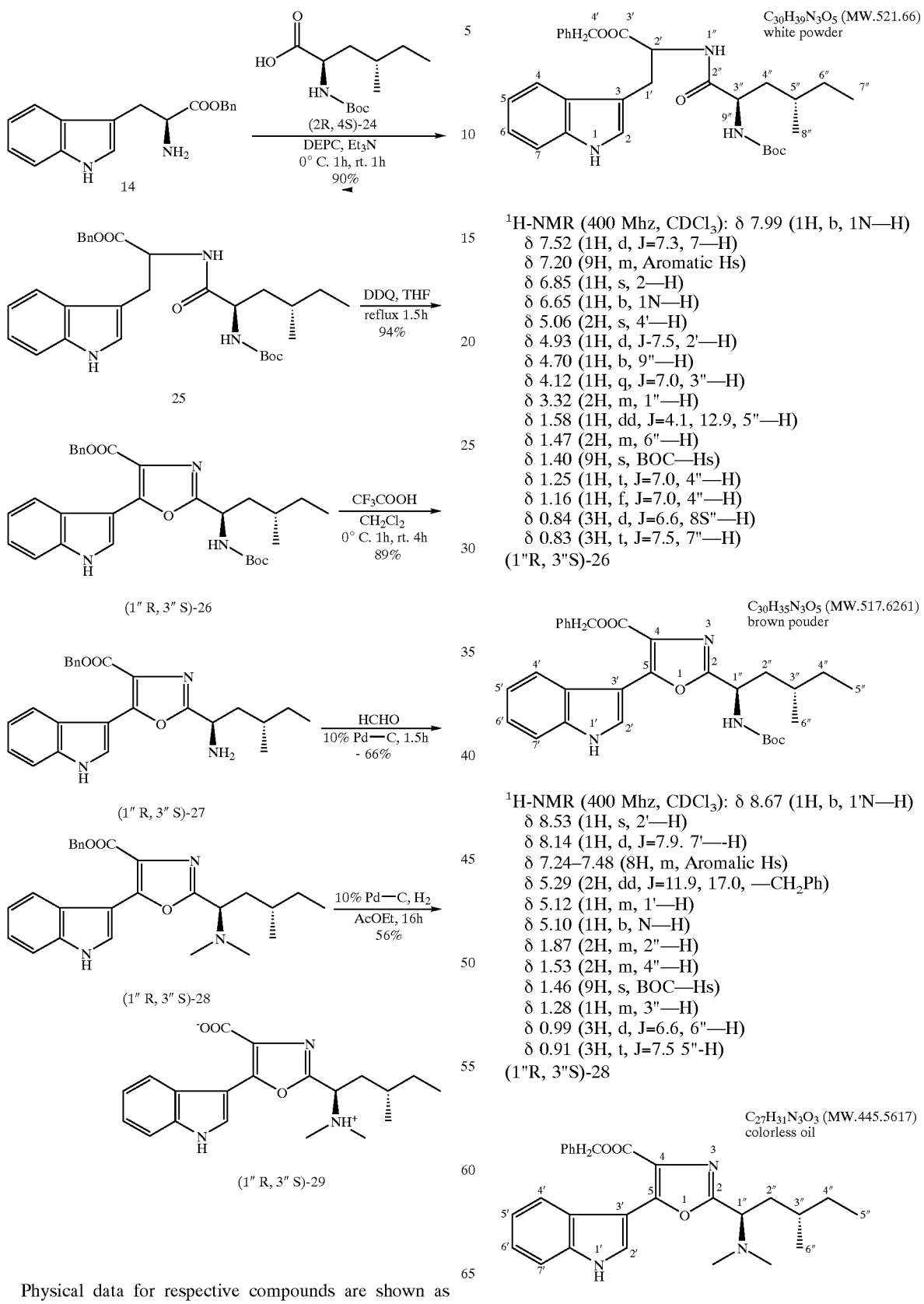

(Compound 25)

$^1$H-NMR (400 Mhz, CDCl$_3$): δ 7.99 (1H, b, 1N—H)
  δ 7.52 (1H, d, J=7.3, 7—H)
  δ 7.20 (9H, m, Aromatic Hs)
  δ 6.85 (1H, s, 2—H)
  δ 6.65 (1H, b, 1N—H)
  δ 5.06 (2H, s, 4'—H)
  δ 4.93 (1H, d, J-7.5, 2'—H)
  δ 4.70 (1H, b, 9"—H)
  δ 4.12 (1H, q, J=7.0, 3"—H)
  δ 3.32 (2H, m, 1"—H)
  δ 1.58 (1H, dd, J=4.1, 12.9, 5"—H)
  δ 1.47 (2H, m, 6"—H)
  δ 1.40 (9H, s, BOC—Hs)
  δ 1.25 (1H, t, J=7.0, 4"—H)
  δ 1.16 (1H, f, J=7.0, 4"—H)
  δ 0.84 (3H, d, J=6.6, 8S"—H)
  δ 0.83 (3H, t, J=7.5, 7"—H)
(1"R, 3"S)-26

$^1$H-NMR (400 Mhz, CDCl$_3$): δ 8.67 (1H, b, 1'N—H)
  δ 8.53 (1H, s, 2'—H)
  δ 8.14 (1H, d, J=7.9, 7'—H)
  δ 7.24–7.48 (8H, m, Aromalic Hs)
  δ 5.29 (2H, dd, J=11.9, 17.0, —CH$_2$Ph)
  δ 5.12 (1H, m, 1'—H)
  δ 5.10 (1H, b, N—H)
  δ 1.87 (2H, m, 2"—H)
  δ 1.53 (2H, m, 4"—H)
  δ 1.46 (9H, s, BOC—Hs)
  δ 1.28 (1H, m, 3"—H)
  δ 0.99 (3H, d, J=6.6, 6"—H)
  δ 0.91 (3H, t, J=7.5 5"-H)
(1"R, 3"S)-28

Physical data for respective compounds are shown as follows.

$^1$H-NMR (400 MHz, CDCl$_3$): δ 9.15 (1H, b, 1'N—H)
δ 8.70 (1H, d, J=3.0, 2'—H)
δ 8.15 (1H, m, 7'—H)
δ 7.43 (3H, m, 4'-6'—H)
δ 7.29 (5H, m, —Ph)
δ 5.43 (2H, dd, J=12.5, 14.6, —CH$_2$Ph)
δ 4.04 (1H, t, J=7.5, 1'—H)
δ 2.39 (6H, s, N(CH$_3$)$_2$)
δ 2.05 (1H, m, 2"—H)
δ 1.84 (1H, m, 2"—H)
δ 1.46 (2H, m, 4"—H)
δ 1.22 (1H, m, 3"—H)
δ 0.89 (3H, d, J=6.6, 6"—H)
δ 0.88 (3H, t, J=7.4. 5"—H)

(1"R, 3"S)-29

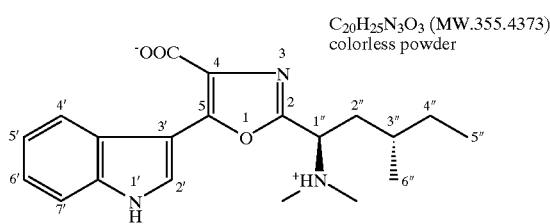

C$_{20}$H$_{25}$N$_3$O$_3$ (MW.355.4373)
colorless powder

IR (KBr): ν [cm$^{-1}$]=3421, 2962, 1597, 1385, 754
$^1$H-NMR (400 MHz, CDCl$_3$): δ 8.67 (1H, s, 2'—H)
δ 8.09 (1H, d, J=7.5, 7'—H)
δ 7.42 (1H d, J=7.6, 4'—H)
δ 7.14 (2H, m, 5', 6'—H)
δ 3.91 (1H, dd, J6.3, 8.8, 1"—H)
δ 2.36 (6H, s, N(CH$_3$)$_2$)
δ 1.96 (2H, m, 2"—H)
δ 1.49 (1H, m, 4"—H)
δ 1.41 (1H, m, 4"—H)
δ 1.21 (1H, m, 3"—H)
δ 0.90 (3H, d, J=6.8, 6"—H)
δ 0.89 (3H, t, J=7.4, 5"—H)
$^{13}$C-NMR (400 MHz, CDCl$_3$): 163.71 f(s), 160.71(s), 159.13(s), 152.42(s), 137.73(s), 131.49(s), 130.10(s), 129.61(s),
123.19(s), 121.60(s), 121.46(s), 112.74(s), 61.99(s), 42.21(s), 42.10(s), 38.74(s), 32.92(s), 29.96(a), 19.78(s), 11.37(s)

EXAMPLE 3

Synthesis of (1"S,3"R)-indole

Similar to Example 1, (1"s,3"R)-indole is prepared from tryptophan ester and (2R,4S)-homoisoleucine in the Preparation Example 3 according to the following synthetic route.

Scheme 7: Synthetic route of (1" S, 3" R) - indole

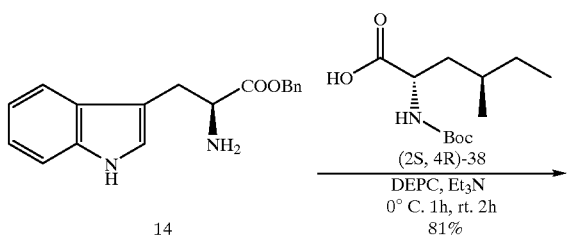

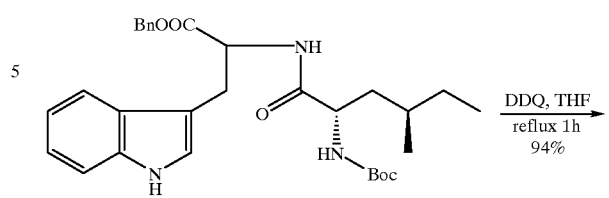

39

[α]$^{24}$$_D$ - 5.92 (c = 0.950, CHCl$_3$)

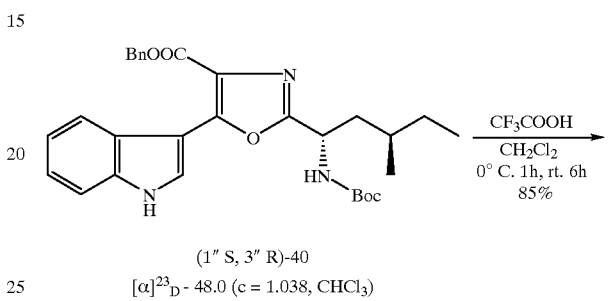

(1" S, 3" R)-40

[α]$^{23}$$_D$ - 48.0 (c = 1.038, CHCl$_3$)

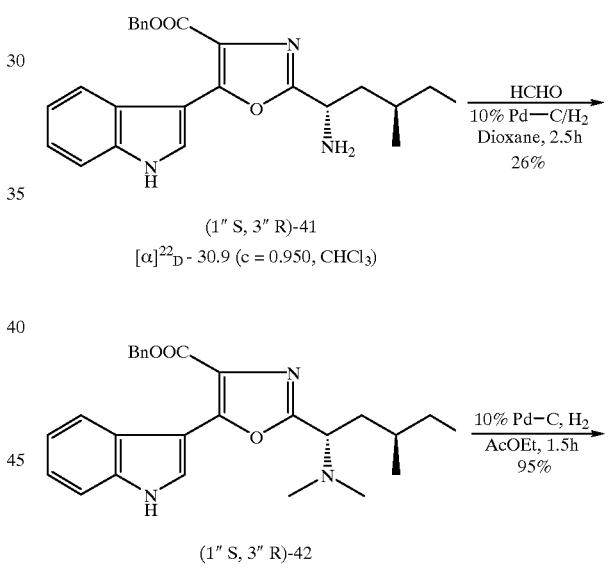

(1" S, 3" R)-41

[α]$^{22}$$_D$ - 30.9 (c = 0.950, CHCl$_3$)

(1" S, 3" R)-42

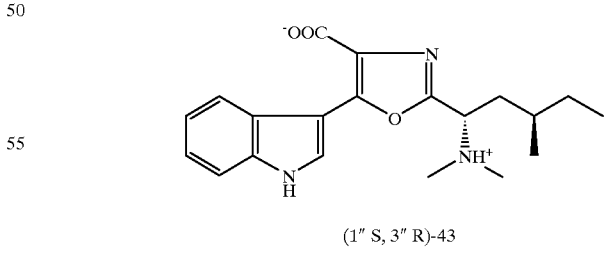

(1" S, 3" R)-43

[α]$^{23}$$_D$ - 21.1 (c = 0.870, MeOH)

Physical data for respective compounds are shown as follows.

(Compound 39)

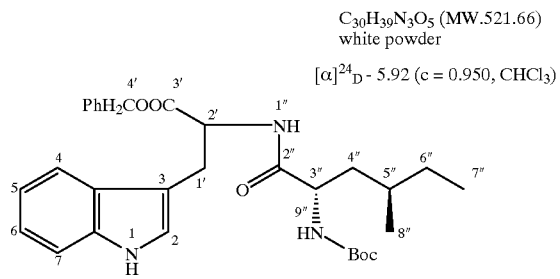

C30H39N3O5 (MW.521.66)
white powder
$[\alpha]^{24}_D$ - 5.92 (c = 0.950, CHCl3)

¹H-NMR (400 Mhz, CDCl3): δ 8.02 (1H, b, 1N—H)
δ 7.52 (1H, d, J=7.8, 7—H)
δ 7.21 (9H, m, Aromatic Hs)
δ 6.86 (1H, s, 2—H)
δ 6.54 (1H, b, 1"N—H)
δ 5.06 (2H, s, 4'—H)
δ 4.94 (1H, d, J=7.8, 2'—H)
δ 4.74 (1H, b, 9"—H)
δ 4.10 (1H, b, 3"—H)
δ 3.32 (2H, d, J=4.9, 1'—H)
δ 1.56 (1H, m, 5"—H)
δ 1.46 (9H, s, BOC—HS)
δ 1.26 (1H, t, J=7.0, 4"—H)
δ 1.16 (1H, f, J=70, 4"—H)
δ 0.85 (3H, d, J=6.6, 8"—H)
δ 0.83 (3H, t, J=7.4, 7"—H)

(1"S, 3"R)-40

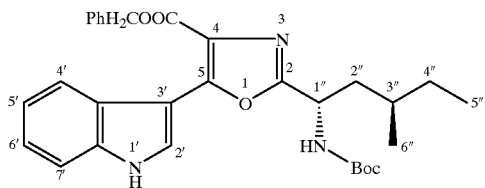

C30H35N3O5 (MW.517.6261)
brown powder
$[\alpha]^{23}_D$ - 48.0 (c = 1.038, CHCl3)

IR (KBr): ν [cm⁻¹]=3276, 2962, 1685, 1593

(1"S, 3"R)-41

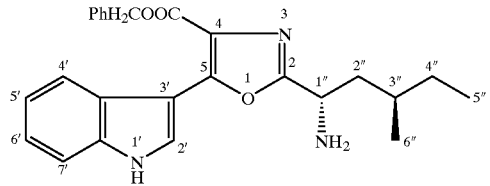

C25H27N3O3 (MW.417.5081)
brown crystal
$[\alpha]^{22}_D$ - 30.9 (c = 0.950, CHCl3)

IR (KBr): ν [cm⁻¹]3274, 2958, 1707, 1593

(1"S, 3"R)-42

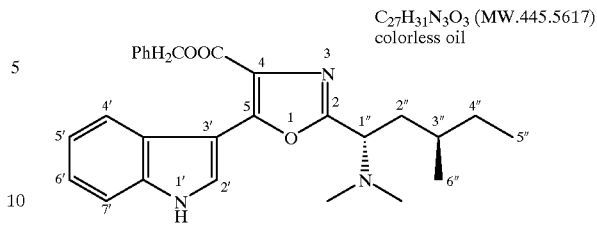

C27H31N3O3 (MW.445.5617)
colorless oil

¹H-NMR (400 MHz, CDCl3): δ 9.15 (1H, b, 1'N—H)
δ 8.70 (1H, d, J=2.9, 2'—H)
δ 8.16 (1H, m, 7'—H)
δ 7.43 (3H, m, 4'~6'—H)
δ 7.30 (5H, m, —Ph)
δ 5.43 (2H, dd, J=12.3, 15.2, —CH2Ph)
δ 4.03 (1H, ?, 1"—H)
δ 2.39 (6H, s, N(CH3)2)
δ 2.06 (1H, m, 2"—H)
δ 1.80 (1H, m, 2"—H)
δ 1.50 (1H, m, 4"—H)
δ 1.43 (1H, m, 4"—H)
δ 1.23 (1H, m, 3"—H)
δ 0.89 (3H, d, J=6.6, 6"—H)
δ 0.89 (3H, t, J=7.3, 5"—H)

(1"S, 3"R)-43

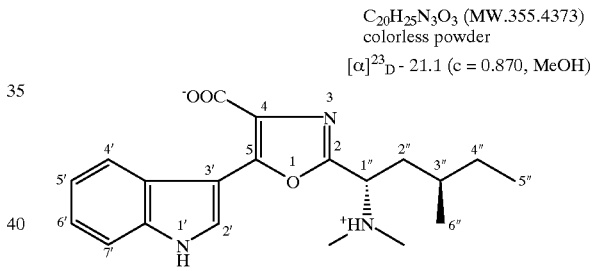

C20H25N3O3 (MW.355.4373)
colorless powder
$[\alpha]^{23}_D$ - 21.1 (c = 0.870, MeOH)

IR (KBr) ν [cm⁻¹]=3400, 2960, 1591, 1458, 1389, 744

EXAMPLE 4

Synthesis of (1"R,3"R)-indole

Similar to Example 1, (1"R,3"R)-indole is prepared from tryptophan ester and (2R,4R)-homoisoleucine in the Preparation Example 4 according to the following synthetic route.

Scheme 8: Synthetic route of (1" S, 3" R) - indole

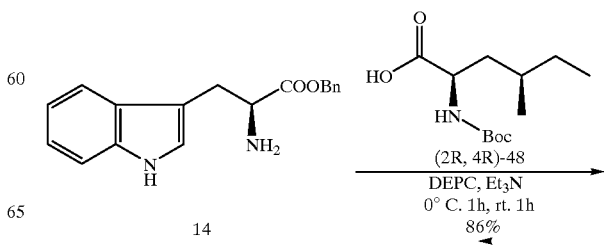

14

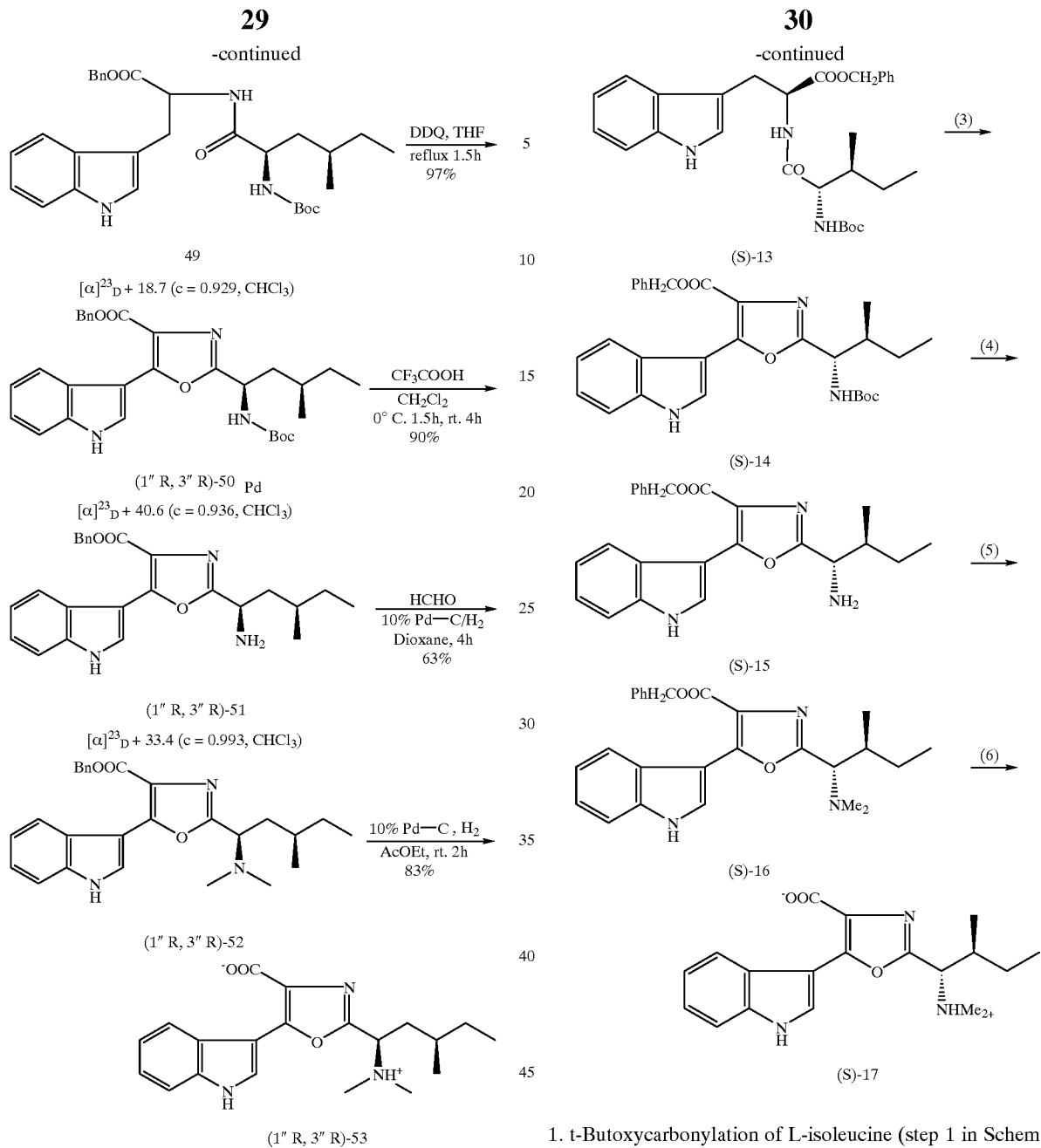

EXAMPLE 5

Synthesis of Stereoisomeric Indole Compound From Tryptophan Ester and L-isoleucine Scheme 9:
Synthetic route of stereoisomeric indole compound from tryptophan ester and L-isoleucine

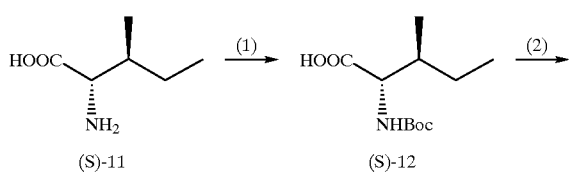

1. t-Butoxycarbonylation of L-isoleucine (step 1 in Scheme 9)

3.00 mg (22.87 mmol) of L-isoleucine (S)-11 is introduced in a 300 ml egg plant type flask and dissolved by adding 21 ml of 1N-NaOH, Furthermore, 15 ml of water, 15 ml of dioxane and 5.49 mg (25.15 mmol) of $Boc_2O$ are added and stirred at room temperature for 5 hours, and additional 2.70 mg (12.37 mmol) of $Boc_2O$ are added and stirred at room temperature for 13 hours. The reaction solution is washed for three times with 30 ml of ether, pH is adjusted to 2–3 by adding citric acid to an aqueous layer in an ice bath, and thereafter it is washed twice with 50 ml of diethyl ether, extracted twice with 30 ml of ethyl acetate, washed for 5 times with 20 ml of water, dried with sodium sulfate and distilled off the solvent, to obtain 4.69 g (yield; 88.7%) of a Boc form (S)-12 of L-isoleucine as colorless oil.

2. Condensation of tryptophan-O-benzyl ester with Boc form of L-isoleucine (step 2 in Scheme 9)

After 0.60 g (1.81 mmol) of tryptophan benzyl ester hydrochloride is introduced in a 100 ml egg plant type flask and argon displacement is carried out, 30 ml of anhydrous THF is added and stirred. Also, 0.48 g (1.94 mmol) of the Boc form (S)-12 of L-isoleucine is introduced in an another flask, subjected to argon displacement and dissolved in 10 ml of anhydrous THF, which is added into the 100 ml egg plant type flask. It is cooled to 0° C. in an ice bath, and 0.58 ml (3.88 mmol) of a condensing agent, DEPC (diethylphosphoryl cyanide) and 0.60 ml (3.59 mmol) of triethylamine are added dropwise, and stirred at 0° C. for 1 hour and thereafter at room temperature for 1 hour. 50 ml of ethyl acetate is added to the reaction solution, which is washed with an aqueous saturated sodium hydrogencarbonate solution and a saturated saline solution, dried with anhydrous sodium sulfate and distilled off the solvent under a reduced pressure. 1.28 g of the obtained brown oil is purified with a silica gel column (60 g of $SiO_2$, ethyl acetate/hexane=1:2) and thereafter recrystallized from ethyl acetate and hexane, to obtain 888.4 mg (yield; 96.5%) of an intended condensate, dipeptide (S)-13 as white needle crystals.

3. DDQ oxidation of dipeptide (S)-13 (step 3 in Scheme 9)

1.50 g (2.94 mmol) of the condensate, dipeptide (S)-13, is introduced in a 200 ml egg plant type flask, subjected to argon displacement, and dissolved in 75 ml of anhydrous THF by adding said THF thereto. 1.31 g (5.77 mmol) of DDQ (2,3-dichloro-5,6-dicyanobenzoquinone) recrystallized from benzene is added and heated at reflux for 3 hours. The solvent of the reaction solution is distilled off, and 200 ml of ethyl acetate and 20 ml of water are added to the residue to carry out extraction, and thereafter the reaction solution is washed with an aqueous saturated sodium hydrogencarbonate solution and a saturated saline solution, dried with anhydrous magnesium sulfate and distilled off the solvent. 1.52 g of the obtained residue is purified with a silica gel column (90 g of $SiO_2$, ethyl acetate/hexane=1:3), to obtain 1.46 g (98.3%) of crude crystals. They are recrystallized from ethyl acetate and n-hexane, to obtain 746.9 mg (50.2%) of an intended cyclized form (S)-14 as white crystals.

4. De-t-butoxycarbonylation of cyclized form (S)-14 (step 4 in Scheme 9)

200 mg (0.40 mmol) of the cyclized form (S)-14 is introduced in a 30 ml two-necked egg plant type flask, dissolved in 5.0 ml (6.49 mmol) of dichloromethane and cooled to 0° C. with an ice bath, to which trifluoroacetjc acid is added and stirred at room temperature until the raw materials being disappeared. The reaction solution is cooled again to 0° C., neutralized with an aqueous saturated sodium hydrogencarbonate solution, distilled off dichloromethane and extracted with ethyl acetate, and thereafter an organic layer is washed with an aqueous saturated sodium chloride solution, dried with anhydrous sodium sulfate and magnesium sulfate, and distilled off the solvent under a reduced pressure, to obtain 185.6 mg of the residue. It is purified with a silica gel column (15 g of $SiO_2$, ethyl acetate/hexane=1:3), to obtain 143.5 mg (93.3%) of a cyclized form (S)-15, which is furthermore recrystallized from ethyl acetate and n-hexane, to obtain 109.0 mg (68.0%) of white crystals.

$C_{24}H_{25}N_3$ $O_3$ (MW.403.48), mp.137–138° C. $[\alpha]_D^{21.5}$–41.6 (c=0.58. $CHCl_3$) IR(KBr) v $[cm^{-1}]$=3282, 2962, 1707, 1593, 1458, 1389, 1360, 1281, 1244, 1192, 1144, 1074, 958, 744, 698, 418

5. Dimethylation of cyclized form (S)-15 (step 5 in Scheme 9)

298.0 mg (0.74 mmol) of the cyclized form (S)-15 is introduced in a 100 ml egg plant type flask and dissolved by adding 14 ml of 37% formaldehyde, 8.0 ml of acetic acid and 6.0 ml of 1,4-dioxane, to which 300 mg of 10% Pd-C is added with cooling in an ice bath and then hydrogen displacement is carried out. Thereafter, the ice bath is removed and stirring is carried out at room temperature for 2.5 hours. Ethanol is added to the reaction solution, Pd-C is removed by filtration, and the filtrate is concentrated. 967.7 mg of the residue is obtained, which is purified with a silica gel column (45 g of $SiO_2$, ethyl acetate/hexane=1:2), to obtain 216.2 mg (yield; 67.9%) of an intended white amorphous dimethyl form (S)-16.

$C_{26}H_{29}N_3$ $O_3$, $[\alpha]_D^{19}$–60.4 (c=0.33, $CHCl_3$) IR(KBr) v $[cm^{-1}]$=3406, 2964, 2931, 2675, 2829, 2783, 1707, 1589, 1458, 1389, 1331, 1281, 1244, 1190, 1136, 1074, 958, 744, 698

6. Debenzylzation of dimethyl form (8)-16 (step 6 in Scheme 9)

87.0 mg of the dimethyl form (S)-16 is introduced in a 50 ml egg plant flask and dissolved by adding 4.0 ml of ethyl acetate, to which 170 mg of 10% Pd-C is added with ice cooling, subjected to hydrogen displacement, and stirred at room temperature for 2 hours. Ethanol is added to the reaction solution, Pd-C is removed by filtration, and the filtrate is concentrated, to obtain 64.3 mg (yield; 93.5%) of an almost pure intended compound as powders. Furthermore, dichloromethane is added to the residue, and insoluble fractions are washed with ethyl ether, to obtain 24.8 mg (yield; 36.0%) of a pure intended compound (S)-17.

$C_{19}H_{23}N_3$ $O_3$, $[\alpha]_D^{20}$–61.0 (c=0.30, MeOH) IR(KBr) v $[cm^{-1}]$=3855, 3413, 2966, 2927, 2875, 2789, 1601, 1523, 1458, 1396, 1244, 1122, 951, 816, 742

II. Synthesis of Deamino Form of Stereoisomeric Compound (deaminomartefragin)

Synthetic examples of deamino forms of the indole compounds according to the invention are illustrated as follows. Before synthesis of the compound according to the invention, synthesis of a raw material thereof, 4-methylhexanoic acid, is illustrated in Preparation Examples 5 and 6, and synthetic examples using it are illustrated in Example 6.

In the following description, demino isomers of the indole compounds of the formula (1) are denoted as compounds 55 and 56; tryptophan of the formula (2) is denoted as compound 14; 4-methylhexanoic acid of the formula (3) is denoted as the compound S-6, R-32; and the amide form compound of the formula (4) is denoted as the compound 54.

PREPARATION EXAMPLE 5

Synthesis of Optically Active (S)-4-maethylhexanoic acid (S-6)

Optically active (S)-4-methylhexanoic acid is obtained from an optically active methylbutanol as a raw material by carrying out the Scheme 1 in the above-mentioned synthetic route of (2S,4S)-homoisoleucine (I. Synthesis for amino forms of indole compounds, Preparation Example 1) to the reaction step (5).

PREPARATION EXAMPLE 6

Synthesis of Optically Active (R)-4-methylhexanoic acid (R-32)

Optically active (R)-4-methylhexanoic acid is obtained from (S)-citronellol as a raw material by carrying out the Scheme 3 in the above-mentioned synthetic route of (2S, 4R)-homoisoleucine (I. Synthesis for amino forms of indole compounds, Preparation Example 3) to the reaction step (3).

33

(S)-4-methylhexanoic acid can be also prepared similar to the above-mentioned Preparation Example 6, in the case that (R)-citronellol being used as a raw material.

Next, synthetic example of indole compounds, deaminomartefragins (compounds 55 and 56) from tryptophan ester (compound 14) and 4-methylhexanoic acid (compound S-6) is illustrated.

EXAMPLE 6

Synthesis of Deaminomartefragin

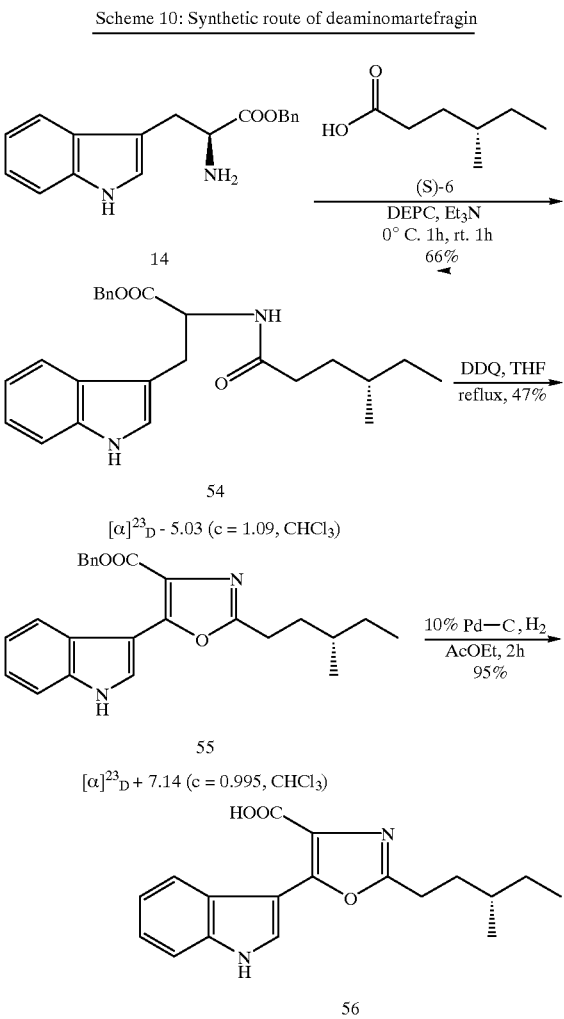

1. Synthesis of compound 54

While (S)-4-methylhexanoic acid (1.0 g, 1.1 equivalents) and diethylphosphoryl cyanide (DEPC, 2.07 ml, 2.0 equivalents) are added to a solution of L-tryptophan benzyl ester hydrochloride (2.31 g, 7.0 mmol) in THF (100 ml) and stirred at 0° C., triethylamine (2–34 ml, 2.4 equivalents) is added and stirred at 0° C. for further 1 hour. After concentrating the reaction solution under a reduced pressure, ethyl acetate is added to the residue. The ethyl acetate solution is washed by adding saturated sodium hydrogencarbonate solution and thereafter washed with 10% hydrochloric acid and a saturated saline solution. An organic layer is dried with anhydrous sodium sulfate and distilled off the solvent under a reduced pressure, to obtain a crude product. The crude product is recrystallized from an ethyl acetate:n-hexane mixed solvent (1:1), to obtain a compound 54 (2.54 g, yield: 89%).

34

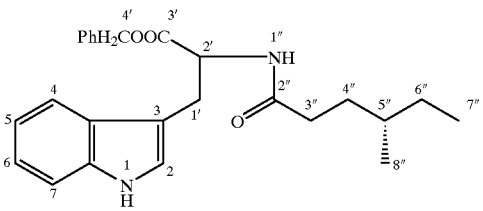

$C_{25}H_{30}N_2, O_3$ (MW.406.23); colorless powder; mp. 80–81° C. (ethyl acetate: n-hexane, 1:1) $[\alpha]_D^{23}$:−5.03(c=1.09, CHCl$_3$) IR (neat): ν [cm$^{-3}$]3300 (—NH), 3112, 2959,1732 (—COO),1651(—CONH), 519, 1456, 1379, 1354, 741, 697 $^1$H-NMR (400 Mhz, CDCl$_3$): δ 8.59 (1H, broad, 1N—H) 7.53 (1H, d, J=7.8, 7—H), 7.21 (9H, m, aromatic-H), 6.74 (1H, d, J=1.7, 2—H), 6.12 (1H, d, J=7.8, 1"N—H) 5.09 (2H, dd, J=12.2, 19.5, '—H), 5.03 (1H, m, 2'—H), 3.32 (2H, dd, J=2.0, 5.4, 1'—H), 2.13 (2H, m, 3"—H), 1.61 (1H, m, 4"—H), 1.38 (1H, m, 4"—H), 1.29 (2H, m, 6"—H), 1.10 (1H, m, 5"—H) 0.84(3H, d, J=7.1, 8"—H), 0.82 (3H, t, J=6.2, 7"—H)

2. Synthesis of compound S5 [deamino form of indole compound of the formula (1) wherein R being benzyl group]

The compound 54 (500 mg, 1.23 mmol) is dissolved in THE (50 ml), to which 2,3-dichloro-5,6-dicyanobenzoquinone (DDQ, 698 mg, 2.5 equivalents) is added and heated at reflux for 1 hour. After the reaction solution is cooled, water is added and TRF is distilled off under a reduced pressure. Ethyl acetate is added to the obtained residue, to carry out extraction. An organic layer is washed with a saturated sodium hydrogencarbonate solution, then with a saturated saline solution, and thereafter dried with anhydrous sodium sulfate. The solvent is distilled off under a reduced pressure, and the obtained residue is purified with a silica gel column chromatography (silica gel, ethyl acetate:n-hexane 1:5), to obtain an almost pure compound 55 (232 mg, yield; 47%). The compound 55 is recrystallized furthermore from ethyl acetate.

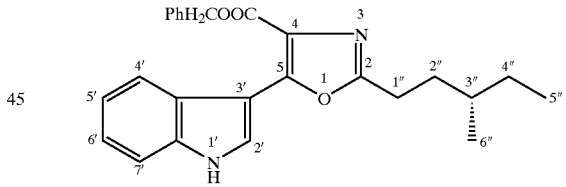

$C_{25}H_{26}N_2O_3$ (MW. 402.19); colorless powder mp.138.5–139.5° C. (ethyl acetate) $[\alpha]_D^{23}$:+7.14 (c=1.00, CHCl$_3$). IR(neat): ν [cm$^{-1}$]3323, 2960, 1684 (CO), 1604, 1570, 1280, 1246, 1203, 1140, 1076, 785, 746

$^1$H-NMR (400 MHz, CDCl$_3$): δ 8.71 (1H, d, J=2.9, 2'—H) 8.59 (1H, broad, 1N—H), 8.18–8.13 (1H, m, 7'—H), 7.45 (3H, m, 4', 5', 6'—H), 7.31(5H, m, —Ph), 5.43 (2H, s, —CH$_2$ Ph), 2.92 (2H, m, 1"—H), 1.93(1H, m, 2"—H), 1.71(1H, m, 2"—H), 14.5 (2H, m, 4"—H), 1.23 (1H, m, 3"—H), 0.96 (3H, d, J=6.5, 6"—H), 0.91 (3H, t, J=7.3, 5"—H)

3. Synthesis of compound 56 [deamino form of indole compound of the formula (1) wherein R being H]

The compound 55 (100 mg, 0.25 mmol) is dissolved in 10 ml of ethyl acetate, to which 100 mg of 10% palladium-carbon is added and stirred at room temperature under a hydrogen atmosphere for 2 hours. Ethanol is added to the reaction solution, the catalyst is filtrated, and thereafter the filtrate is concentrated under a reduced pressure to obtain a crude product (95.4 mg), which is purified with a column chromatography (silica gel, ethyl acetate:methanol 10:1) to obtain a compound 56 (53 mg, yield; 69%).

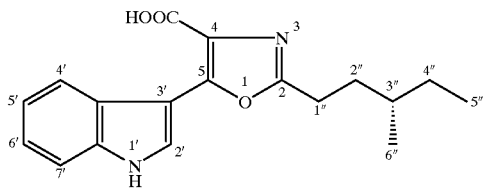

$C_{18}H_{20}N_2O_3$ (MW. 312.15); colorless powder; mp. 181.0–183.0° C. (hydrous ethanol) IR(neat): ν [cm$^{-1}$]3161, 2960, 1676, 1603, 1560, 1458, 1414, 1278, 1130, 1082, 949, 741 $^1$H-NMR (400 MHz, CDCl$_3$): δ 8.64 (1H, s, 2'—H), 8.04 (1H, d, J=8.0, 7'-H), 7.42(1H, d, J=7.3, 4'—H), 7.20–7.13(2H, m, 5' and 6'—H), 2.88–2.74(2H, m, 1"—H), 1.90–1.80 (1H, m, 2"—H), 1.66–1.57 (1H, m, 2"—H), 1.45–1.34 (2H, m, 4"—H), 1.25–1.13(1H, m, 3"—H), 0.92 (3H, d, J=6.6, 6"—H), 0.87 (3H, t, J=7.2, 5"—H)

III. Biological Activities of Stereoisomeric Indole Compounds

EXAMPLE 7

Effect of Stereoisomeric Indole Compounds Against Lipid peroxidation of Microsome in Rat Liver (1) Determination of peroxidized lipid 10 μl of microsome fraction (protein concentration; 30–50 mg/ ml) prepared from rat liver and 10 μl of a solution of a compound to be tested in ethanol are added to 0.5 ml of 0.1 M Tris hydrochloride buffer (pH7.5) containing 14 mM MgCl$_2$, which is mixed and preincubated at 37° C. for 5 minutes. Then, 10 μl of 0.2M adenosine diphosphate, 10 μl of 12 mM FeSO$_4$, 40 μl of NADPH reproduced system and distilled water are added to make 1 ml, mixed and reacted at 37° C. for 10 minutes. After the reaction, 2 ml of a 15% trichloroacetic acid solution containing 0.375% thiobarbituric acid (TBA) and 0.25N hydrochloric acid is added and reacted in a boiling water bath for 15 minutes, and then amounts of thiobarbituric acid reactive substances including malonic dialdehyde produced by the reaction are determined from absorption at a wavelength of 535 nm. Based on these values, a value for inhibitory action against lipid peroxidation at 50% (IC$_{50}$ value) is obtained.

(2) Test results

As the result of determination about inhibitory action against lipid peroxidation of respective stereoisomeric indole compounds, (1"S, 3"S)-19 in Example 1, (1"R, 3"S)-29 in Example 2, (1"R, 3"R)-53 in Example 4, (1"S, 3"R)-43 in Example 3 and (S)-17 in Example 5, IC$_{50}$ values of homoisoleucine types, (S,S) former (R,S) form, (R,R) form and (S,R) form are 1.07, 1.10, 1.24 and 1.10 μg/ml respectively, as shown in the following Table. Furthermore, IC$_{50}$ values of hoinoisoleucine (S) form is 1.89 μg/ml, which means slightly weak activity.

| Compound | Inhibiting Concentration (IC$_{50}$ μg/ml) |
|---|---|
| (1"S, 3"S)-19 | 1.07 |
| (1"R, 3"S)-29 | 1.10 |
| (1"R, 3"R)-53 | 1.24 |
| (1"S, 3"R)-43 | 1.10 |
| (S)-17 | 1.89 |

EXAMPLE 8

Effect of indole compounds against lipad peroxidation of microsome in rat liver (1) Determination of peroxidated lipid It is carried out according to the method described in Example 7.

(2) Test results

Inhibitory action against lipid peroxidation of respective indole compounds, i.e., deaminomartefragin compound 56) in Example 6 and synthetic; (1"S, 3"S) Martefragin A (the above-mentioned compound 19), are compared and studied. As the result, IC$_{50}$ values of and synthetic (1"S, 3"S) Martefragin A are 0.33 μg/m and 1.35 μg/ml respectively, as shown in the following Table, thus deaminomartefragin exhibits stronger activity.

| Compound | Inhibiting Concentration (IC$_{50}$ μg/ml) |
|---|---|
| Deaminomartefragin (compound 56) | 0.33 |
| Synthetic Martefragin A [compound(1"S,3"S)-19] | 1.35 |

EFFECT OF THE INVENTION

It becomes possible to obtain various novel indole compounds according to the invention by a novel synthetic method comprising condensation of tryptophan with a stereoisomeric α-amino acid or 4-methylhexanoic acid to form an amide form and subsequent oxidative cyclization of the amide form to form an oxazole ring at once. Obtained alkaloids having an indole ring and an oxazole ring have physiological activities such as inhibitory action against lipid peroxidation and they can be utilized as materials for pharmaceutics and cosmetics and the like. Furthermore, deamino forms of the indole compounds have higher physiological activities such as inhibitory action against lipid peroxidation than the amino forms.

What is claimed is:

1. A synthetic stereoisomeric indole compound of R-form or S-form of the formula (1) or a salt thereof

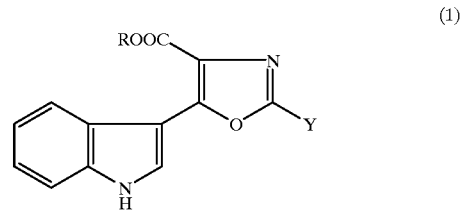

wherein, Y represents the group

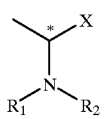

wherein, X represents alkyl group having 1–5 carbon atom(s) (the alkyl group may be optionally substituted with hydroxyl group, carboxyl group, amino group, methylthio group, mercapto group, guanidyl group, imidazolyl group, or benzyl group), and $R_1$ and $R_2$ represent each independently hydrogen atom, alkyl group, aralkyl group, cycloalkyl group or aryl group; or

R represents hydrogen atom, alkyl group, aralkyl group, cycloalkyl group, aryl group, monovalent metal atom, amine or ammonium; and the symbol '*' represents a position of an asymmetric carbon atom, provided that when X is —$CH_2$—$C(CH_3)H$—$CH_2$—$CH_3$, the compound is not the (1″S,3″S) form.

2. A synthetic stereoisomeric indole compound of R-form or S-form of the formula (1a) or a salt thereof

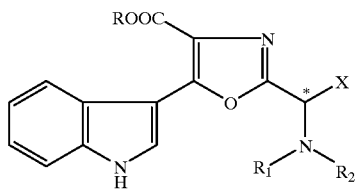
(1a)

wherein, X represents alkyl group having 1–5 carbon atom(s) (the alkyl group may be optionally substituted with hydroxyl group, carboxyl group, amino group, methylthio group, mercapto group, guanidyl group, imidazolyl group, or benzyl group); R represents hydrogen atom, alkyl group, aralkyl group, cycloalkyl group, aryl group, monovalent metal atom, amine or ammonium; and $R_1$ and $R_2$ represent each independently hydrogen atom, alkyl group, aralkyl group, cycloalkyl group or aryl group and the symbol '*' represents a position of an asymmetric carbon atom, provided that when X is —$CH_2$—$C(CH_3)H$—$CH_2$—$CH_3$, the compound is not the (1″S,3″S) form.

3. A stereoisomeric indole compound of the formula (1b) or a salt therof

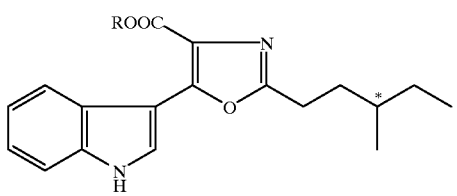
(1b)

wherein, R represents hydrogen atom, alkyl group, aralkyl group, cycloalkyl group, aryl group, monovalent metal atom, amine or ammonium; and the symbol '*' represents a position of an asymmetric carbon atom.

4. A process for preparing a stereoisomeric indole compound of the formula (1)

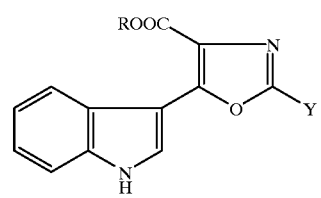
(1)

by condensing tryptophan of the formula (2)

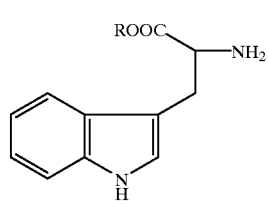
(2)

with an acid of the formula (3)

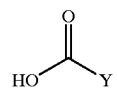
(3)

to obtain a compound of the formula (4),

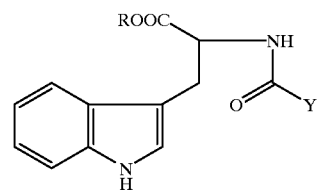
(4)

and subjecting the compound of the formula (4) to cyclization,
wherein, Y represents the group

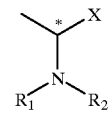

wherein, X represents alkyl group having 1–5 carbon atom(s) (the alkyl group may be substituted with hydroxyl group, carboxyl group, amino group, methylthio group, mercapto group, guanidyl group, imidazolyl group or benzyl group), and $R_1$ and $R_2$ represent each independently hydrogen atom, alkyl group, aralkyl group, cycloalkyl group or aryl group; or Y represents the group

R represents hydrogen atom, alkyl group, aralkyl group, cycloalkyl group, aryl group, monovalent metal atom, amine or ammonium; and the symbol '*' represents a position of an asymmetric carbon atom.

5. A process for preparing a stereoisomeric indole compound of the formula (1a)

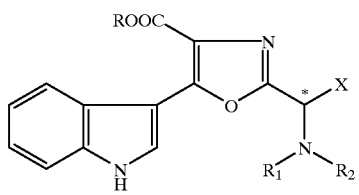
(1a)

by condensing tryptophan of the formula (2)

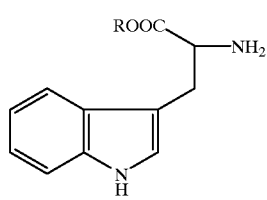
(2)

with a stereoisomeric α-amino acid of the formula (3a)

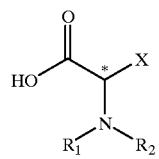
(3a)

to obtain a compound of the formula (4a),

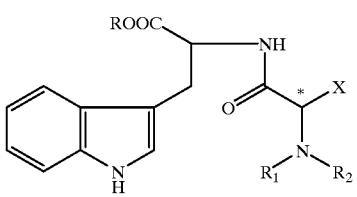
(4a)

and subjecting the compound of the formula (4a) to cyclization, wherein, X represents alkyl group having 1–5 carbon atom(s) (the alkyl group may be substituted with hydroxyl group, carboxyl group, amino group, methylthio group, mercapto group, guanidyl group, imidazolyl group or benzyl group); R represents hydrogen atom, alkyl group, aralkyl group, cycloalkyl group, aryl group, monovalent metal atom, amine or ammonium; $R_1$ and $R_2$ represent each independently hydrogen atom, alkyl group, aralkyl group, cycloalkyl group or aryl group; and the symbol '*' represents a position of an asymmetric carbon atom.

6. A process for preparing a stereoisomeric indole compound of the formula (1b)

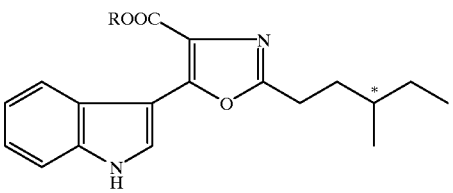
(1b)

by condensing tryptophan of the formula (2)

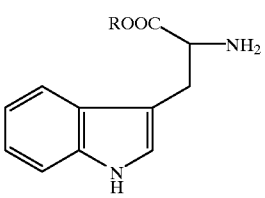
(2)

with an carboxylic acid of the formula (3b)

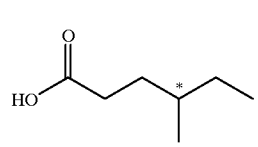
(3b)

to obtain a compound of the formula (4b),

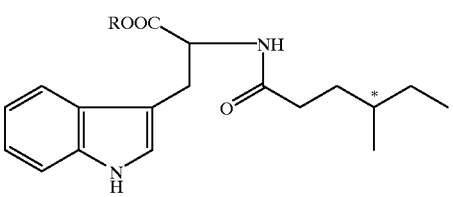
(4b)

and subjecting the compound of the formula (4b) to cyclization, wherein, R represents hydrogen atom, alkyl group, aralkyl group, cycloalkyl group, aryl group, monovalent metal atom, amine or ammonium; and the symbol '*' represents a position of an asymmetric carbon atom.

7. A lipid peroxidation inhibitor comprising as the active ingredient the synthetic stereoisomeric indole compound or a salt thereof according to claim 1.

8. A synthetic stereoisomeric indole compound of R-form or S-form according to claim 2, of the formula

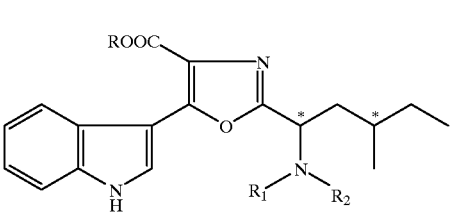
(1a')

wherein, R represents hydrogen atom, alkyl group, aralkyl group, cycloalkyl group, aryl group, monovalent metal atom, amine or ammonium; and $R_1$ and $R_2$ represent each independently hydrogen atom, alkyl group, aralkyl group, cycloalkyl group or aryl group and the symbol '*' represents a position of an asymmetric carbon atom, excluding (1"S,3"S) form of said compound.

9. A lipid peroxidation inhibitor comprising as the active ingredient the synthetic stereoisomeric indole compound or a salt thereof according to claim 2.

10. A lipid peroxidation inhibitor comprising as the active ingredient the synthetic stereoisomeric indole compound or a salt thereof according to claim 8.

11. A lipid peroxidation inhibitor comprising as the active ingredient the stereoisomeric indole compound or a salt thereof according to claim 3.

12. The synthetic stereoisomeric indole compound of claim 1, where said compound is in the (1"S,3"R) form.

13. The synthetic stereoisomeric indole compound of claim 1, where said compound is in the (1"R,3"R) form.

14. The synthetic stereoisomeric indole compound of claim 1, where said compound is in the (1"R,3"S) form.

15. The synthetic stereoisomeric indole compound of claim 1, where said compound is in the (1"S,3"S) form.

16. The synthetic stereoisomeric indole compound of claim 2, where said compound is in the (1"S,3"R) form.

17. The synthetic stereoisomeric indole compound of claim 2, where said compound is in the (1"R,3"R) form.

18. The synthetic stereoisomeric indole compound of claim 2, where said compound is in the (1"R,3"S) form.

19. The synthetic stereoisomeric indole compound of claim 2, where said compound is in the (1"S,3"S) form.

* * * * *